United States Patent [19]

Diana

[11] 3,984,467
[45] Oct. 5, 1976

[54] ANTHELMINTIC 1-(SUBSTITUTED PHENYL)-3-ALKANIMIDOYL UREAS

[75] Inventor: Guy D. Diana, Stephentown, N.Y.

[73] Assignee: Sterling Drug Inc., New York, N.Y.

[22] Filed: Nov. 21, 1973

[21] Appl. No.: 418,087

Related U.S. Application Data

[63] Continuation-in-part of Ser. No. 15,875, March 2, 1970, Pat. No. 3,830,839, which is a continuation-in-part of Ser. No. 711,235, March 7, 1968, Pat. No. 3,629,455.

[30] Foreign Application Priority Data

Mar. 3, 1969 United Kingdom............... 11308/69

[52] U.S. Cl. .................. 260/553 A; 260/243 B; 260/247.1 R; 260/247.2 R; 260/268 R; 260/293.73; 260/293.74; 260/293.75; 260/293.77; 260/326.8; 260/326.83; 260/326.85; 260/332.2 R; 260/347.3; 260/347.7; 260/465 D; 260/481 R; 260/482 R; 260/552 R; 424/248; 424/267; 424/274; 424/275; 424/285; 424/298; 424/304; 424/311; 424/322

[51] Int. Cl.² ........................................ C07C 127/19
[58] Field of Search ................................ 260/553 A

[56] References Cited

UNITED STATES PATENTS

| | | |
|---|---|---|
| 3,146,262 | 8/1964 | Schäfer et al. ............... 260/553 A |
| 3,547,937 | 12/1970 | Diana ......................... 260/553 A X |
| 3,629,455 | 12/1971 | Diana ......................... 260/553 A X |
| 3,790,631 | 2/1974 | Diana ......................... 260/553 A |
| 3,830,839 | 8/1974 | Diana ......................... 260/553 A |
| 3,898,277 | 8/1975 | Duerr et al. ................. 260/553 A X |

FOREIGN PATENTS OR APPLICATIONS

| | | |
|---|---|---|
| 1,407,241 | 11/1965 | France |
| 1,357,946 | 11/1964 | France |
| 1,045,170 | 10/1966 | United Kingdom |

Primary Examiner—Robert V. Hines
Assistant Examiner—Thomas A. Waltz
Attorney, Agent, or Firm—Frederik W. Stonner; B. Woodrow Wyatt

[57] ABSTRACT

The compounds of this invention are novel imidoylureas having anthelmintic activity and imidoylthioureas having antifertility activity. They are prepared by the reaction of appropriate amidines with appropriate isocyanates or isothiocyanates.

5 Claims, No Drawings

ANTHELMINTIC 1-(SUBSTITUTED PHENYL)-3-ALKANIMIDOYL UREAS

This application is a continuation-in-part of copending application, Ser. No. 15,875, filed Mar. 2, 1970, now U.S. Pat. No. 3,830,839, issued Aug. 20, 1974, in turn a continuation-in-part of copending application, Ser. No. 711,235, filed Mar. 7, 1968, now U.S. Pat. No. 3,629,455, issued Dec. 21, 1971.

This invention relates to novel imidoylureas and imidoylthioureas and to their preparation.

In one aspect of this invention, there is provided novel 1-phenyl-3-alkanimidoylureas having the formula

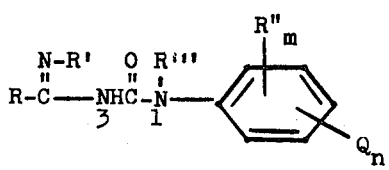

I where R is alkyl or $R_1R_2N$—Y, where Y is alkylene and $R_1$ and $R_2$, which can be the same or different, each are lower-alkyl or benzyl, or $R_1$ and $R_2$ taken together with the nitrogen form a heterocyclic ring of the group consisting of morpholino, thiomorpholino, piperidino, pyrrolidino, piperazino, N-lower-alkylpiperazino and N-phenylpiperazino; R' and R''' each are hydrogen or lower-alkyl; R'' is lower-alkyl; Q is one or two to n of the same or different substituents of the group consisting of lower-alkoxy, phenyl-lower-alkoxy, lower-alkanoyloxy, hydroxy, di(lower-alkyl)amino, lower-alkanoylamino, amino, lower-alkylsulfonyl, lower-alkylsulfinyl, lower-alkylthio, trihalomethyl, trihalomethoxy, nitro, cyano and halo; n is an integer from 1 to 5; and m is an integer from 0 to (5-n).

Another aspect of this invention is the provision of novel 1-phenyl-3-alkanimidoylureas of the formula

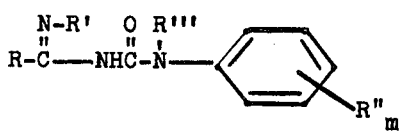

II where R is alkyl or $R_1R_2N$—Y, where Y is alkylene and $R_1$ and $R_2$, which can be the same or different, each are lower-alkyl or benzyl, or $R_1$ and $R_2$ taken together with the nitrogen form a heterocyclic ring of the group consisting of morpholino, thiomorpholino, piperidino, pyrrolidino, piperazino, N-lower-alkylpiperazino and N-phenylpiperazino; R' and R''' each are hydrogen or lower-alkyl; R'' is lower-alkyl; and m is an integer from 0 to 5.

Another aspect of this invention is the provision of novel alkanimidoylthioureas having the formula

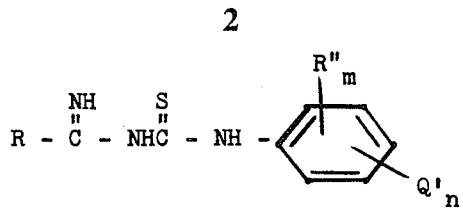

Formula III where R is alkyl or $R_1R_2N$—Y, where Y is alkylene and $R_1$ and $R_2$, which can be the same or different, each are lower-alkyl or benzyl, or $R_1$ and $R_2$ taken together with the nitrogen form a heterocyclic rin of the group consisting of morpholino, thiomorpholino, piperidino, pyrrolidino, piperazino, N-lower-alkylpiperazino and N-phenylpiperazino; R'' is lower-alkyl; Q' is one or two to n of the same or different substituents of the group consisting of lower-alkoxy, benzyloxy, lower-alkanoyloxy, hydroxy, di(lower-alkyl)amino, lower-alkanoylamino, amino, lower-alkylmercapto, trihalomethoxy, trihalomethyl, nitro, cyano and halo; n is an integer from 1 to 5; and m is an integer from 0 to (5-n).

Another aspect of this invention is the provision of novel imidoylureas having the formula

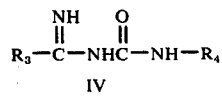

IV where $R_3$ is phenyl when $R_4$ is alkyl or nitrophenyl; and $R_3$ is 5-nitro-2-furyl when $R_4$ is alkyl, nitrophenyl or halophenyl.

It will be understood that when $R_4$ of formula IV is halophenyl the phenyl ring can bear one, or two to five of the same or different halo substituents which can be attached at any of the available positions and when there are a plurality of halo substituent, these halo substituents can occur in any position combinations relative to each other.

Another aspect of this invention is the provision of novel imidoylureas having the formula

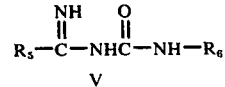

V where $R_5$ is alkyl; and $R_6$ is cyclohexyl or 2-thienyl.

It will be understood that the substituents represented by R'' in formulas I, II and III as defined hereinabove can be attached to the phenyl ring at any of the available positions and when there are a plurality of substituents R'', these substituents can be the same or different and can occur in any of the position combinations relative to each other.

The compounds of formula I and formula II are prepared by the following methods:

By reacting, in a suitable solvent, that is, a solvent which is essentially inert under the conditions of the reaction, an amidine of the formula

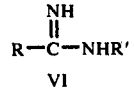

VI with an isocyanate of the formula

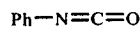

VII or alternatively, where R''' is lower-alkyl, a carbamyl chloride of the formula

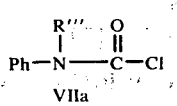

VIIa where R and R' have the meaning hereinbefore defined for R and R' of formula I and formula II; and Ph is

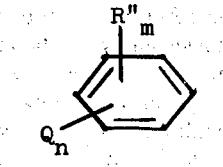

where Q is one or two to $n$ of the same or different substituents of the group consisting of lower-alkoxy, phenyl-lower-alkoxy, lower-alkanoyloxy, di(lower-alkyl)amino, lower-alkanoylamino, lower-alkylsulfonyl, lower-alkylsulfinyl, lower-alkylthio, trihalomethyl, trihalomethoxy, nitro, cyano and halo; and R'', $m$ and $n$ have the meaning hereinbefore defined for R'', $m$ and $n$ of formula I; or Ph is

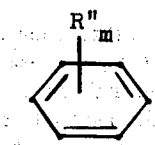

where R'' and $m$ have the meaning hereinbefore defined for R'' and $m$ of formula II.

The reaction is preferably carried out by reacting an amidine of formula VI with an equivalent amount of an isocyanate of formula VII in a non-hydroxylic solvent, alternatively, an equivalent amount of a carbamyl chloride of formula VIIa, for example, acetone or benzene, at temperatures ranging from about 5° to about 15°C., for about one-half hour, and then allowing the temperature of the reaction mixture to rise to room temperature. The reaction is usually complete after about one hour. When a carbamyl chloride of formula VIIa is the reactant, it is preferred that at least one equivalent of a suitable acid-acceptor, e.g., triethylamine or pyridine, is added in order to take up the hydrogen chloride formed during the course of the reaction. However, the reaction can be performed successfully in the absence of said acid-acceptor if desired.

The exothermic reaction can be carried out at temperatures ranging from about 0 to about 80°C. However, the resulting desired compounds of formula I, where R' is hydrogen, can react further with the unreacted isocyanate, represented by formula VII, or carbamyl chloride, represented by formula VIIa especially at elevated temperatures, to form undesired side products. In order to avoid or minimize such further reaction, the reaction is preferably carried out initially at temperatures below room temperature using approximately equimolar amounts of the appropriate amidine and isocyanate or carbamyl chloride.

The compounds of formula I and formula III where Q and Q' respectively include one or more amino and/or hydroxy substituents are prepared, by well known catalytic hydrogenation procedures, from the corresponding compounds where Q and Q' include one or more nitro and/or benzyloxy substituents respectively, whereby said substituents are converted to amino and/or hydroxy substituents.

The catalytic hydrogenation is carried out at room temperature in an inert solvent, e.g. ethyl alcohol, under essentially neutral conditions in the presence of a suitable catalyst, e.g. Raney nickel or palladium on charcoal, and at about atmospheric pressure and the hydrogenation is stopped after a stoichiometric amount of hydrogen has reacted.

It will be understood that the substituents represented by Q and Q' as defined hereinabove can be attached to the phenyl ring at any of the available positions and where there are a plurality of substituents Q and/or Q', these substituents Q and/or Q' respectively can be the same or different and can occur in any of the position combinations relative to each other.

The amidine in its free base form employed as starting material in the above described process is prepared from its corresponding salt, e.g. the hydrochloride by reacting this salt with a stoichiometric amount of an appropriate base in a suitable solvent, for example, sodium acetonide in acetone, triethylamine in chloroform, or sodium methoxide in benzene. It is preferred to use the resulting solution of the amidine directly in the next step but the amidine can be isolated by conventional techniques before use.

Amidine salts belong to a generally known class of compounds and can be readily prepared from nitriles by methods well known in the art of chemistry. Thus, a desired amidine can be obtained by conversion of the corresponding nitrile of the formula

VIII to the salt of the corresponding imino-ether followed by treatment with an amine of the formula

IX where R and R' have the meaning hereinbefore defined for R and R' of formula I.

The following general procedure illustrates the method that can be used for the preparation of the salt of the amidine of formula VI.

Dry hydrogen chloride gas is passed through an icebath cooled solution of 2 moles of the intermediate nitrile in 100 ml. absolute ether and 2.1 moles of dry methyl alcohol until 2.6 moles is absorbed and the resulting solution is allowed to stand at about 5°C. for about 3 days. The resulting solid imino-methylether hydrochloride is ground to a paste under absolute ethyl alcohol and added to a solution of 2.2 moles of the intermediate amine in 400 ml. absolute ethyl alcohol and the solution is stirred at room temperature for 3 hours and then kept at about 5°C. for about 16 hours during which time the amidine hydrochloride generally precipitates in crystalline form and can be isolated by filtration and used without further purification in the next step. Alternatively the amidine hydrochloride can be recrystallized from a suitable solvent before use.

The nitriles of formula VIII where R is $R_1R_2$—N—Y, that is $R_1R_2$—N—Y—C ≡ N (Formula VIIIa), employed as starting materials in the hereinbefore described process are prepared by conventional procedures from the corresponding halonitriles having the formula X—Y—C ≡ N (X), where X is iodo, by reaction with an appropriate amine of the formula $R_1R_2$NH. The amines of formula $R_1R_2$NH belong to a class of well known compounds and are readily available.

The iodonitriles of formula X are obtained by a conventional procedure from the corresponding halonitrile having the formula X—Y—C ≡ N (Xa), where X is bromo or chloro, by reaction with sodium iodide.

The nitriles having the formula Xa are generally known compounds or are prepared from known compounds by conventional procedures. For example, haloalkanoic acids of the formula

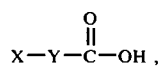

where X is bromine or chlorine, are converted by conventional procedures to the corresponding amides of formula

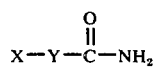

which are then dehydrated by known procedures, e.g. with phosphorus pentachloride, to the nitriles of formula Xa. Alternatively they can be prepared from known dibasic carboxylic acids, $Y(CO_2H)_2$, by well known procedures, for example, conversion of the appropriate acid to its dimethyl ester followed by reduction, for example, with sodium in absolute ethyl alcohol, to the corresponding diol, further reacting the diol with a halogenating agent, for example, hydrobromic acid or phosphorus pentachloride to give the corresponding dihalo compound $Y(X)_2$ and finally reacting the dihalo compound with a metallic cyanide, for example sodium or potassium cyanide, to give the corresponding nitrile of formula Xa.

The nitriles of formula VIII where R is alkyl belong to a well known class of compounds and are known compounds or can be prepared from the corresponding known acids and amides by well known procedures as described above for the preparation of the nitriles of formula Xa. Alternatively they can be prepared by another well known procedure, for example, by reacting an appropriate alkyl halide RX, where X is chloro, bromo or iodo, with a metallic cyanide such as an alkali cyanide, for example, sodium cyanide to give the corresponding nitrile of formula VIII.

The isocyanates of formula VII and the carbamyl chlorides of formula VIIa employed as starting materials in the hereinbefore described process each belong to a well known class of compounds and can be readily prepared by conventional methods, for example, by condensing an amine of the formula

where Ph has the meaning hereinbefore defined for Ph of formula VII and R''' is hydrogen or lower-alkyl, with one equivalent of phosgene in a suitable solvent, for example toluene, to give the corresponding carbamyl chloride (formula VIIA, R''' is H or lower-alkyl), and, when R''' is hydrogen, either heating or distilling the resulting carbamyl chloride, or treating the resulting carbamyl chloride with a suitable acid acceptor, e.g., sodium carbonate, whereupon the isocyanate or formula VII is obtained with concomitant elimination of hydrogen chloride. The resulting corresponding isocyanate or carbamyl chloride can be isolated and purified by standard techniques.

Other well known procedures that can be used for the preparation of the isocyanates of formula VII are the Hoffmann, Curtius, or Lossen rearrangements of appropriate amides, acid azides, or hydroxamic acids respectively obtained by well known procedures from the known corresponding carboxylic acids of the formula

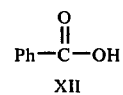

where Ph has the meaning hereinbefore defined for Ph of formula VII.

Compounds having Formulas III, IV and V are prepared by the methods described hereinbefore for the preparation of compounds of Formulas I and II using the appropriate amidines and isocyanates or isothiocyanates as illustrated by the following reaction sequences:

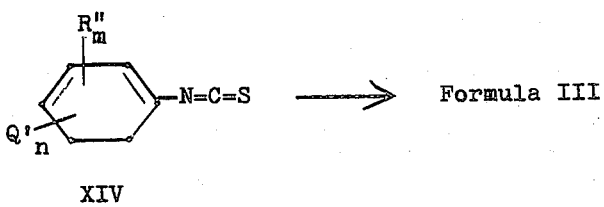

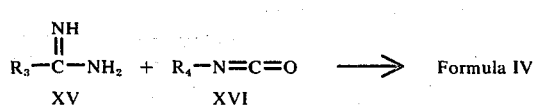

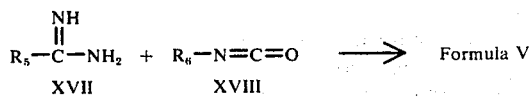

Formula V where R, R'', m, n, $R_3$, $R_4$, $R_5$ and $R_6$ have meanings hereinbefore defined for formulas III, IV and V and Q' is one or two to n of the same or different substituents of the group consisting of lower-alkoxy, benzyloxy, lower-alkanoyloxy, di(lower-alkylamino), lower-alkanoylamino, lower-alkylmercapto, trihalomethoxy, trihalomethyl, nitro, cyano and halo.

The amidines of formulas XIII, XV and XVII employed as starting materials in the hereinbefore described process are prepared from the corresponding nitriles, that is, $R-C \equiv N$ (VIII), $R_3-C \equiv N$ and $R_5-C \equiv N$ respectively using the method described hereinbefore for the preparation of amidines of formula VI.

The nitriles having the formulas $R_3-C \equiv N$ and $R_5-C \equiv N$ used as starting materials in the above process are known compounds.

The isocyanates of formulas XVI and XVIII employed as starting materials in the hereinbefore described process are generally known or are prepared from the corresponding known amines or known carboxylic acids by the conventional methods described hereinbefore for the preparation of the isocyanates of formula VII.

The isothiocyanates of formula XIV employed as starting materials in the hereinbefore described process are generally known compounds and can be prepared by conventional procedures, for example, by reaction of an appropriate aniline with thiophosgene in a manner similar to that described hereinbefore for the preparation of the isocyanate of formula VII.

The carbimidoylureas of our invention exist in tautomeric forms as illustrated by the formulas As with all tautomeric systems, the rate of transformation I ⇌ IA and the ratio I/IA are dependent on the thermodynamic environment, including the state of aggregation, so that measurements by any particular technique do not necessarily have validity except under the conditions of the measurement, thereby, among other consequences, giving rise to problems for any simple designation of the physical embodiments. Thus, measurement of the infrared spectra in potassium bromide admixture and measurement of the nuclear magnetic spectra are not helpful in determining which tautomeric form, I or IA is present or predominates and therefore the names based on structure I are preferred although it is understood that either or both structures I and IA are comprehended.

In a like manner, the carbimidoylureas of Formulas II, III, IV and V also exist in similar tautomeric forms but names based on structures II, III, IV and V are preferred.

Throughout this specification it will be understood that the term "alkyl" means a group preferably having one to fourteen carbon atoms which can be arranged in a straight or branched chain as illustrated, without limiting the generality of the foregoing, by methyl, ethyl, propyl, isopropyl, butyl, isobutyl, heptyl, nonyl, decyl or tetradecyl.

Throughout this specification, the term "alkylene" means a divalent hydrocarbon chain preferably having from one to twelve carbon atoms, which can be arranged in a straight or branched chain, and, without limiting the generality of the foregoing, is illustrated by methylene, 1,2-ethylene, 1,3-propylene, 1,2-(1-methylethylene), 1,4-butylene, 1,12-dodecylene and the like.

Here and elsewhere throughout this specification it will be understood that the terms "lower-alkyl", "lower-alkoxy" and "lower-alkanoyl" each mean a group preferably containing from one to six carbon atoms which can be arranged in a straight or branched chain as illustrated, without limiting the generality of the foregoing, by methyl, ethyl, propyl, isopropyl, butyl, sec-butyl, pentyl, or hexyl for lower-alkyl; methoxy, ethyl, isopropoxy, or hexyloxy for lower-alkoxy; and acetyl, propionyl, trimethylacetyl, and caproyl for lower-alkanoyl.

As used throughout this specification the term "halo" includes chloro, bromo, fluoro and iodo.

The novel cabimidoylureas of the instant invention can exist in either base or acid-addition salt form. The compounds of formulas I, II, III, IV and V in free base form, are converted to the acid-addition salt form by interaction of the base with an acid. In like manner, the free bases can be regenerated from the acid-addition salt form in the conventional manner, that is, by treating the salts with strong aqueous bases, for example alkali metal hydroxides, alkali metal carbonates, and alkali metal bicarbonates. The bases thus regenerated can then be interacted with the same or a different acid to give back the same or a different acid-addition salt. Thus the novel bases and all of their acid-addition salts are readily inter-convertible, and are the full equivalents of each other.

It will thus be appreciated the formulas I, II, III, IV and V not only represent the structural configuration of the bases of formulas I, II, III, IV and V but are also representative of the structural entity which is common to all of our compounds of formulas I, II, III, IV and V whether in the form of the free bases or in the form of the acid-addition salts of the bases. We have found that by virtue of this common structural entity, the bases and their acid-addition salts have inherent pharmacodynamic activity of a type more fully described herein. This inherent pharmacodynamic activity can be enjoyed in useful form for pharmaceutical purposes by employing the free bases themselves or the acid-addition salts formed from pharmaceutically-acceptable

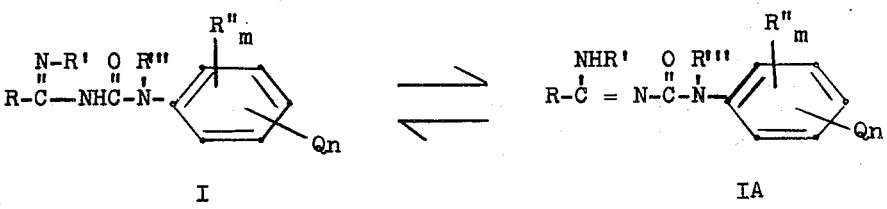

I       IA acids, that is, acids whose anions are innocuous to the animal organism in effective doses of the salts so that beneficial properties inherent in the common structural entity represented by the free bases are not vitiated by side-effects ascribable to the anions.

In utilizing this pharmacodynamic activity of the salts of the compounds of formula I, II, III, IV and V, we prefer of course to use pharmaceutically-acceptable salts. Although water-insolubility, high toxicity, or lack of crystalline character may make some particular salt species unsuitable or less desirable for use as such in a given pharmaceutical application, the water-insoluble or toxic salts can be converted to the corresponding pharmaceutically-acceptable bases by decomposition of the salt with aqueous base as explained above, or alternatively, they can be converted to any desired pharmaceutically-acceptable acid-addition salt by double decomposition reactions involving the anion, for example, by ion-exchange procedures.

Moreover, apart from their usefulness in pharmaceutical applications, our salts are useful as characterizing or identifying derivatives of the free bases or in isolation or purification procedures. Like all of the acid-addition salt, such characterizing or purification salt derivatives can, if desired, be used to regenerate the pharmaceutically-acceptable free bases by reaction of the salts with aqueous base, or alternatively can be converted to a pharmaceutically-acceptable acid-addition salt by, for example, ion-exchange procedures.

It will be appreciated from the foregoing that all of the acid-addition salts of our new bases are useful and valuable compounds, regardless of considerations of solubility, toxicity, physical form, and the like, and are accordingly within the purview of the instant invention.

The novel feature of the compounds of the invention, then, resides in the concept of the bases and cationic forms of the new imidoylureas and imidoylthioureas and not in any particular acid moiety or acid anion associated with the salt forms of our compounds; rather, the acid moieties or anions which can be associated in the salt forms are in themselves neither novel nor critical and therefore can be any acid anion or acid-like substance capable of salt formation with bases. In fact, in aqueous solutions, the base form or water-soluble acid-addition salt form of the compounds of the invention both possess a common protonated cation or ammonium ion.

Thus the acid-addition salts discussed above and claimed herein are prepared from any organic acid, inorganic acid (including organic acids having an inorganic group therein), or organo-metallic acid as exemplified by organic mono and polycarboxylic acids, such as found, for example, in Beilstein's Organische Chemie, 4th ed., Volumes III, IV, IX, X, XIV, XVII, XIX, XXI, XXII, and XXV; organic mono- and polysulfonic and -sulfinic acids, such as found, for example, in Beilstein Volumes VI, XI, XVI, and XXII; organic phosphonic and phosphinic acids such as found, for example, in Beilstein Volumes XI and XVI; organic acids or arsenic and antimony, such as found, for example, in Beilstein Volume XVI; organic heterocyclic carboxylic, sulfonic, and sulfinic acids, such as found, for example, in Beilstein Volumes XVIII, XXII, and XXV; acidic ion-exchange resins; and inorganic acids of any acid forming element or combination of elements, such as found in Mellor, Comprehensive Treatise or Inorganic and Theoretical Chemistry, Longman's Green and Co., New York, N.Y. Volumes I-XVI. In addition, other salt-forming compounds which are acidic in their chemical properties but which are not generally considered as acids in the same sense as carboxylic or sulfonic acids are also considered to be among the numerous acids which can be used to prepare acid-addition salts of the compounds of the invention. Thus there is also comprehended acidic phenolic compounds, such as found, for example, in Volume VI of Beilstein, acidic compounds having "activated" or acidic hydrogen atoms, as for example, picrolonic acid, or barbituric acid derivatives having an acidic proton, such as found, for example, in Cox et al. Medicinal Chemistry, Vol. IV, John Wiley and Sons, Inc., New York, N.Y. (1959). Also comprehended as salt forming agents are so-called Lewis acids which lack a pair of electrons in the outer "electron shell" and react with basic compounds having an unshared pair of electrons to form salts, for example boron trifluoride.

Representative acids for the formation of the acid-addition salts include formic acid, acetic acid, trifluoroacetic acid, isobutyric acid, alpha-mercaptopropionic acid, malic acid, fumaric acid, oxalic acid, succinic acid, succinamic acid, glutamic acid, tartaric acid, citric acid, pamoic acid, lactic acid, glycolic acid, gluconic acid, saccharic acid, ascorbic acid, penicillin, benzoic acid, 4-methoxybenzoic acid, phthalic acid, salicylic acid, acetylsalicylic acid, anthranilic acid, 1-naphthalenecarboxylic acid, cinnammic acid, cyclohexanecarboxylic acid, mandelic acid, tropic acid, crotonic acid, acetylene dicarboxylic acid, sorbic acid, pyromucic acid, cholic acid, pyrenecarboxylic acid, 2-pyridinecarboxylic acid, 3-indoleacetic acid, quinic acid, sulfamic acid, methanesulfonic acid, ethanesulfonic acid, isethionic acid, benzenesulfonic acid, p-toluenesulfonic acid, benzenesulfinic acid, butylarsonic acid, diethylphosphonic acid, p-aminophenylarsinic acid, phenylstibnic acid, phenylphosphinous acid, methane-phosphonic acid, phenylphosphinic acid, acidic resins, hydrofluoric acid, hydrochloric acid, hydrobromic acid, hydriodic acid, perchloric acid, nitric acid, sulfuric acid, phosphoric acid, hydrocyanic acid, phosphotungstic acid, molybdic acid, phosphomolybdic acid, pyrophosphoric acid, arsenic acid, picric acid, picrolonic acid, barbituric acid, boron trifluoride, and the like.

The acid-addition salts are prepared either by dissolving the free base in an aqueous solution containing the appropriate acid and isolating the salt by evaporating the solution, or by reacting the free base and acid in an organic solvent, in which case the salt separates directly or can be obtained by concentration of the solution.

The compounds of formulas I, II, IV and V of this invention has been tested in dogs by standard chemotherapeutic evaluation procedures described hereinbelow and were found to possess anthelmintic activity, in particular anti-hookworm activity. In addition, some of these compounds also possess anti-tapeworm activity. They are therefore useful as anthelmintic agents, in particular as anti-hookworm agents.

TEST PROCEDURE FOR THE DETERMINATION OF ANTHEMINTIC ACTIVITY

Anti-hookworm Activity: Both naturally infected and artificially infected mongrel dogs were used in the test. The naturally infected dogs carried a burden of two kinds of hookworm (*Uncinaria stenocephala* and *Ancylostoma caninum*). The artificially infected dogs were treated with sufficient hookworm (*Ancylostoma caninum*) larvae approximately 1 month prior to treatment with a test agent to insure that a mature infection would be present at the time of the test. Food was withheld from the dogs for a minimum of 5 hours prior to, and for three to 5 hours after, each administration of the test agent. Equal doses of the test agent were administered orally to from two to three dogs, infected naturally or artificially, one to two doses per dog per day for from 1 to 5 consecutive days. the dogs were sacrificed 5 to 8 days post-first medication and the intentines were searched for worms.

The above described test procedure can also be used in the determination of anthelmintic activity where the host is infected by other intestinal vermiform parasites, for example tapeworm.

The carbimidoylureas of formulas I, II, IV and V of this invention were found to reduce or eliminate the helminth burden from hookworm infested dogs when administered in the dose range of from 10 to 125 mg./kg. (calculated on the basis of the free base). The number of doses administered ranged from one to two per day for from 1 to 5 consecutive days, depending on the severity of the helminth infestation.

The actual determination of the numerical biological data definitive for a particular compound of formulas I, II, IV and V is readily determined by standard test procedures by technicians versed in pharmacological test procedures, without the need for any extensive experimentation.

The carbimidoylureas of formulas I, II, IV and V can be incorporated in unit dosage form as tablets or capsules for oral administration either alone or in combination with suitable adjuvants such as calcium carbonate, starch, lactose, talc, magnesium stearate, gum acacia, and the like.

Furthermore, if it is desired to broaden the spectrum of activity and/or to secure the advantages of potentiated action, the formulations can have incorporated in them, in addition to the compounds of formulae I, II, IV and V, one or more other orally effective anthelmintic and/or potentiating agents. For example such agents, without limiting the generality of the foregoing, can be illustrated by piperazine in the case of ascariasis and enterobiasis; thiabendazole in the case of ascariasis, strongyloidiasis, trichuriasis and trichinosis; pyrvinium in the case of enterobiasis and strongyloidiasis; quinacrine, aspidium, bithionol and niclosamide in the case of tapeworm infections; bithionol in case of trematode infections and biphenium in the case of ascariasis and trichuriasis.

Still further the carbimidoylureas of formulas I, II, IV and V can be formulated for oral administration in aqueous alcohol, glycol, or oil solutions or oil-water emulsions in the same manner as conventional medicinal substances are prepared; they can be formulated for oral use with foodstuffs or admixed with foodstuffs for veterinary use.

The compounds of formulas I, II, IV and V are preferably administered orally and the amount of a particular compound to be administered, either by itself or as the essentially active ingredient in a formulation will range from about 10 to about 125 mg. (calculated on the basis of the free base) per kilogram of body weight of the helminth infested animal and the number of doses to be administered will range from one to two per day for from 1 to 5 consecutive days, depending on the severity of the helminth infestation.

The compounds of formula III of this invention have been tested in rats by a standard endocrinological evaluation procedure described hereinbelow and were found to possess antifertility activity. They are therefore useful as antifertility agents.

TEST PROCEDURE OF THE DETERMINATION OF ANTIFERTILITY ACTIVITY

Mature female rats were medicated daily with the test agent for two days prior to insemination by proven male rats and daily for 6 days after insemination (a total of eight medications). The rats were autopsied 15 days after insemination and their uteri were removed and examined for evidence of pregnancy. The test agents were administered either as suspensions, depending on solubility and dosage level, in ten percent ethyl alcohol-cottonseed oil.

The carbimidoylthioureas of formula III of this invention were found to be effective as antifertility agents when administered either subcutaneously or orally to female rats in the dose range of from 50 to 100 mg/kg × 8 days (calculated on the basis of the free base) according to the procedure described above.

The actual determination of the numerical biological data definitive for a particular compound of formula III is readily determined by standard test procedures by technicians versed in pharmacological test procedures, without the need for any extensive experimentation.

The compounds of formula III of this invention can be prepared for use by dissolving under sterile conditions a salt form of the compounds in water (or an equivalent amount of a nontoxic acid if the free base is used), or in a physiologically compatible aqueous medium such as saline, and stored in ampoules for intramuscular injection. Alternatively, they can be incorporated in unit dosage form as tablets or capsules for oral administration either alone or in combination with suitable adjuvants such as calcium carbonate, starch, lactose, talc, magnesium stearate, gum acacia, and the like. Still further the compounds can be formulated for oral administration in aqueous alcohol, glycol, or oil solutions or oil-water emulsions in the same manner as conventional medicinal substances are prepared.

The molecular structures of the compounds of this invention were assigned on the basis of the method of their synthesis and study of their infrared spectra, and confirmed by the correspondence between calculated and found values for the elementary analysis for representative examples.

The following examples will further illustrate the invention without, however, limiting it thereto;

EXAMPLE 1

1-(4-Chlorophenyl)-3-(pentanimidoyl)urea

To a stirred mixture, prepared by reacting 4.6 g. sodium with 300 ml. dry acetone at room temperature, was added 27.2 g. valeramidine hydrochloride in one portion and stirring was continued for 20 minutes. To the resulting mixture was added dropwise, during 1½ hours, a solution of 30.7 g. 4-chlorophenyl isocyanate in 100 ml. dry acetone with stirring and external cooling in order to prevent the exothermic reaction from heating the mixture above room temperature. Stirring was continued at room temperature for eighteen hours and the mixture was concentrated to dryness under reduced pressure. The residue was taken up in ether and the sodium chloride was removed by filtration. The filtrate was chilled and treated with ethereal hydrogen chloride until acidic and the resulting solid was collected by filtration, washed with ether, and recrystallized from ethyl alcohol to give 34.6 g. of the hydrochloride of 1-(4-chlorophenyl)-3-(pentanimidoyl)urea; m.p. 202°–204°C.

A suspension of 10 g. of the hydrochloride in 100 ml. dry ether was treated with 3 ml. of isopropylamine with stirring. The mixture was allowed to stand for one hour at room temperature, the solids were removed by filtration, and the filtrate was evaporated to dryness under reduced pressure. The residue was crystallized from benzene-hexane to yield 1-(4-chlorophenyl)-3-(pentanimidoyl)urea; m.p. 82°–84°C.

To a stirred solution of 30 g. of the free base in 750 ml. methyl alcohol was added a solution of 30 g. sodium lauryl sulfate in 250 ml. water. After thirty minutes water was added to the solution and the mixture was cooled and filtered to give 40.9 g. 1-(4-chlorophenyl)-3-(pentanimidoyl)urea lauryl sulfate, m.p. 188.5°–189°C. (from ethyl acetate).

Treatment of a benzene solution of the free base with a stoichiometric amount of lactic acid, evaporation to dryness under reduced pressure, and trituration with ether yielded the lactate of 1-(4-chlorophenyl)-3-(pentanimidoyl)urea; m.p. 100°–103°C.

Treatment of an isopropyl alcohol solution of the free base with an aqueous solution of a stoichiometric amount of sulfamic acid, evaporation to dryness under reduced pressure, and recrystallization from isopropyl alcohol yielded the sulfamate of 1-(4-chlorophenyl)-3-(pentanimidoyl)urea; m.p. 143.5°–145°C.

To 300 ml. stirred water, cooled to 5°C. and with continued cooling at 5° to 15°C., was added simultaneously and dropwise, during forty minutes, a solution of 30 g. 1-(4-chlorophenyl)-3-(pentanimidoyl)urea hydrochloride in 600 ml. water and a solution of 23.3 g. disodium 4,4'-methylene-bis(3-hydroxy-2-naphthoate), hereinafter pamoate, in 600 ml. water, such that a slight excess of the pamoate over the hydrochloride was maintained during the addition. The mixture was stirred an additional twenty minutes and the solids were collected by filtration, recrystallization of which from absolute ethyl alcohol yielded 1-(4-chlorophenyl)-3-(pentanimidoyl)urea hemipamoate; m.p. 164°–169°C.

Following a procedure similar to that described in Example 1 but substituting for valeramidine hydrochloride an equivalent amount of the hydrochlorides of the following:
  a. acetamidine
  b. isobutyramidine
  c. 3,7-dimethyloctanamidine
  d. tridecanamidine
  e. pentadecanamidine
there can be obtained respectively the hydrochlorides of the following:
  a. 1-(4-chlorophenyl)-3-(acetimidoyl)urea
  b. 1-(4-chlorophenyl)-3-(isobutyrimidoyl)urea
  c. 1-(4-chlorophenyl)-3-(3,7dimethyloctanimidoyl)urea
  d. 1-(4-chlorophenyl)-3-(tridecanimidoyl)urea
  e. 1-(4-chlorophenyl)-3-pentadecanimidoyl)urea.

EXAMPLE 2

1-(4-Methoxyphenyl)-3-(pentanimidoyl)urea

Following a procedure similar to that described in Example 1 but using 3.39 g. sodium in 200 ml. dry acetone, 20 g. valeramidine hydrochloride and 21.9 g. 4-methoxyphenyl isocyanate in 100 ml. dry acetone, there ws obtained after recrystallization from ethyl alcohol 15.5 g. of the hydrochloride of 1-(4-methoxyphenyl)-3-(pentanimidoyl)urea; m.p. 143.5°–145°C.

EXAMPLE 3

1-(4-Chlorophenyl)-3-(nonanimidoyl)yrea

Following a procedure similar to that described in Example 1 but using 3.9 g. sodium in 300 ml. dry acetone, 28.9 g. nonanamidine hydrochloride, and 23 g. p-chlorophenyl isocyanate in 100 ml. dry acetone, there was obtained after recrystallization from acetonitrile 40.5 g. of the hydrochloride of 1-(4-chlorophenyl)-3-(nonanimidoyl)yrea; m.p. 155°–157°C.

The nonanamidine hydrochloride (m.p. 113°C.) used above was prepared following the general procedure described in Example 11B but substituting for valeronitrile and methylamine an equivalent amount of nonanenitrile and ammonia respectively.

EXAMPLE 4

1-(4-Chlorophenyl)-3-(octanimidoyl)urea

Following a procedure similar to that described in Example 1 but using 2.2 g. sodium in 200 ml. dry acetone, 17.8 g. octanamidine hydrochloride, and 15.3 g. 4-chlorophenyl isocyanate in 100 ml. benzene, there was obtained after recrystallization from acetonitrile 19.7 g. of the hydrochloride of 1-(4-chlorophenyl)-3-(octanimidoyl)urea; m.p. 156°–165°C.

EXAMPLE 5

1-(2-Chlorophenyl)-3-(pentanimidoyl)urea

Following a procedure similar to that described in Example 1 but using 2.3 g. sodium in 250 ml. dry acetone, 13.6 g. valeramidine hydrochloride, and 15.3 g. 2-chlorophenyl isocyanate in 100 ml. dry acetone, there was obtained after recrystallization from isopropyl alcohol-ether 15.4 g. of the hydrochloride of 1-(2-chloropheyl)-3-(pentanimidoyl)yrea; m.p. 132°–134°C.

EXAMPLE 6

1-(4-Chloro-2-nitrophenyl)-3-(pentanimidoyl)urea

A. Following a procedure similar to that described in Example 1 but using 3.4 g. sodium in 300 ml. dry acetone, 20.2 g. valeramidine hydrochloride, and 29.3 g. 4-chloro-2-nitrophenyl isocyanate in 100 ml. dry acetone, there was obtained after recrystallization from absolute ethyl alcohol 21 g. of the hydrochloride of 1-(4-chloro-2-nitrophenyl)-3-pentanimidoyl)urea; m.p. 170°–174°C.

B. The 4-chloro-2-nitrophenyl isocyanate used above was prepared as follows: A solution of 181 g. phosgene in 640 ml. chlorobenzene was chilled, 40 g. 4-chloro-2-nitroaniline was added portionwise with stirring, and the resulting mixture was slowly heated to reflux temperature in a phosgene atmosphere and heating was continued for 3 hours. The solution was evaporated to dryness under reduced pressure and the residue was recrystallized from hexane to give 4-chloro-2-nitrophenyl isocyanate; m.p. 54°–56°C.

Following a procedure similar to that described in Example 6B but substituting for 4-chloro-2-nitroaniline an equivalent amount of the following:
  a. 4-hexyloxyaniline b. 4-(5-phenylpentyloxy)aniline
c. 4-acetoxyaniline
d. 4-acetamidoaniline
e. 4-butyramidoaniline
f. 3-methylsulfinylaniline
g. 4-hexylsulfonylaniline
h. 3-isobutylsulfonylaniline
i. 3-hexylthioaniline
j. 4-(trifluoromethoxy)aniline there can be obtained respectively the following:
a. 4-hexyloxyphenyl isocyanate
b. (5-phenylpentyloxy)phenyl isocyanate
c. 4-acetoxyphenyl isocyanate
d. 4-acetamidophenyl isocyanate
e. 4-butyramidophenyl isocyanate
f. 3-methylsulfinylphenyl isocyanate
g. 4-hexylsulfonylphenyl isocyanate
h. 3-isobutylsulfonylphenyl isocyanate
i. 3-hexylthiophenyl isocyanate
j. 4-(trifluoromethoxy)phenyl isocyanate Following a procedure similar to that described in Example 6A but substituting for 4-chloro-2-nitrophenyl isocyanate an equivalent amount of the following:
a. 4-hexyloxyphenyl isocyanate
b. 4-(5-phenylpentyloxy)phenyl isocyanate
c. 4-acetoxyphenyl isocyanate
d. 4-acetamidophenyl isocyanate
e. 4-butyramidophenyl isocyanate
f. 3-methylsulfinylphenyl isocyanate
g. 4-hexylsulfonylphenyl isocyanate
h. 3-isobutylsulfonylphenyl isocyanate
i. 4-methylsulfonylphenyl isocyanate
j. 4-(trifluoromethoxy)phenyl isocyanate
k. 3-hexylthiophenyl isocyanate
l. 4-methylthiophenyl isocyanate
m. 4-diethylaminophenyl isocyanate
n. pentachlorophenyl isocyanate
o. 2,4-diiodo-5-methoxyphenyl isocyanate
p. 4-bromo-2-methylphenyl isocyanate there can be obtained respectively the hydrochlorides of the following:
a. 1-(4-hexyloxyphenyl)-3-(pentanimidoyl)urea
b. 1-[4-(5-phenylpentyloxy)phenyl]-3-(pentanimidoyl)urea
c. 1-(4-acetoxyphenyl)-3-(pentanimidoyl)urea
d. 1-(4-acetamidophenyl)-3-(pentanimidoyl)urea
e. 1-(4-butyramidophenyl)-3-(pentanimidoyl)urea
f. 1-(3-methylsulfinylphenyl)-3-(pentanimidoyl)urea
g. 1-(4-hexylsulfonylphenyl)-3-(pentanimidoyl)urea
h. 1-(3-isobutylsulfonylphenyl)-3-(pentanimidoyl)urea
i. 1-(4-methylsulfonylphenyl)-3-(pentanimidoyl)urea
j. 1-[4-(trifluoromethoxy)phenyl]-3-(pentanimidoyl)urea
k. 1-(3-hexylthiophenyl)-3-(pentanimidoyl)urea
l. 1-(4-methylthiophenyl)-3-(pentanimidoyl)urea
m. 1-(4-diethylaminophenyl)-3-(pentanimidoyl)urea
n. 1-(pentachlorophenyl)-3-(pentanimidoyl)urea
o. 1-(2,4-diiodo-5-methoxyphenyl)-3-(pentanimidoyl)urea
p. 1-(4-bromo-2-methylphenyl)-3-(pentanimidoyl)urea.

EXAMPLE 7

1-(3,4-Dichlorophenyl)-3-(pentanimidoyl)urea

Following a procedure similar to that described in Example 1 but using 3.39 g. sodium in 200 ml. dry acetone, 20 g. valeramidine hydrochloride, and 27.6 g. 3,4-dichlorophenyl isocyanate in 100 ml. dry acetone, there was obtained after recrystallization from acetone 10.5 g. of the hydrochloride of 1-(3,4-dichlorophenyl)-3-(pentanimidoyl)urea; m.p. 177°–179°C.

EXAMPLE 8

1-(4-Chlorophenyl)-3-(hexanimidoyl)urea

Following a procedure similar to that described in Example 1 but using 3.2 g. sodium in 200 ml. dry acetone, 21. g. hexanamidine hydrochloride, and 21.4 g. 4-chlorophenyl isocyanate in 100 ml. dry acetone, there was obtained after recrystallization from acetone 13.9 g. of the hydrochloride of 1-(4-chlorophenyl)-3-(hexanimidoyl)urea; m.p. 175°–179°C.

EXAMPLE 9

1-(4-Nitrophenyl)-3-(pentanimidoyl)urea

Following a procedure similar to that described in Example 1 but using 3.39 g. sodium in 200 ml. dry acetone, 20 g. valeramidine hydrochloride, and 21.9 g. 4-nitrophenyl isocyanate in 100 ml. dry acetone, there was obtained after recrystallization from methyl alcohol 10.8 g. of the hydrochloride of 1-(4-nitrophenyl)-3(-pentanimidoyl)urea; m.p. 187°–191°C.

EXAMPLE 10

1-(4-Aminophenyl)-3-(pentanimidoyl)urea

A solution of 30 g. of 1-(4-nitrophenyl)-3-(pentanimidoyl)urea hydrochloride (see Example 9) in 300 ml. ice-cold water was treated with 8 g. sodium hydroxide in 40 ml. water. The mixture was extracted with ether and the ethereal solution was dried over calcium sulfate and evaporated to dryness. The residue was taken up in 400 ml. absolute alcohol and hydrogenated over Raney nickel at 392 pounds pressure and at room temperature until the hydrogen uptake was complete. The catalyst was removed by filtration and the solvent was removed under reduced pressure at 50°C. to give after recrystallization successively from ether and benzene 13.5 g. of 1-(4-aminophenyl)-3-(pentanimidoyl)urea; m.p. 102°–103°C.

EXAMPLE 11

1-(4-Chlorophenyl)-3-(N-methylpentanimidoyl)urea

A. Following a procedure similar to that described in Example 1 but using 5.25 g. sodium in 200 ml. dry acetone, 37.8 g. N-methylvaleramidine hydrochloride, and 38.4 g. p-chlorophenyl isocyanate in 100 ml. dry acetone, there was obtained after recrystallization from ethyl alcohol 15.0 g. of the hydrochloride of 1-(4-chlorophenyl)-3-(N-methylpentanimidoyl)urea; m.p. 154°–158°C.

B. The N-methylvaleramidine hydrochloride used above was prepared as follows: 20.8 g. valeronitrile in 8 g. dry methyl alcohol and 12 ml. absolute ether was treated, with ice-bath cooling, with hydrogen chloride gas until 9.1 g. has been absorbed and left to stand at 5°C. for 60 hours. The resulting solid iminomethylether was collected and added to 7.8 g. methylamine in 50 ml. absolute ethyl alcohol and the solution was stirred at room temperature for 20 hours, filtered, and the filtrate was evaporated to dryness. The residue was slurried in ether and the ether was decanted. The resulting N-methylvaleramidine was used without further purification in the next step.

Following a procedure similar to that described in Example 11B but substituting for methylamine an equivalent amount of the following:
  a. isopropylamine
  b. hexylamine
there can be obtained respectively the hydrochlorides of the following:
  a. N-isopropylvaleramidine
  b. N-hexylvaleramidine.

Following a procedure similar to that described in Example 11A but substituting for N-methylvaleramidine an equivalent amount of the hydrochlorides of:
  a. N-isopropylvaleramidine
  b. N-hexylvaleramidine
there can be obtained respectively the hydrochlorides of the following:
  a. 1-(4-chlorophenyl-3-(N-isopropylpentanimidoyl)urea
  b. 1-(4-chlorophenyl)-3-(N-hexylpentanimidoyl)urea.

EXAMPLE 12

1-(3-Chlorophenyl)-3-(pentanimidoyl)urea

Following a procedure similar to that described in Example 1 but using 6.9 g. sodium in 300 ml. dry acetone, 41.1 g. valeramidine hydrochloride, and 46.2 g. 3-chlorophenyl isocyanate in 200 ml. dry acetone, there was obtained after recrystallization from acetone 27.1 g. of tjhe hydrochloride of 1-(3-chlorophenyl)-3-(pentanimidoyl)urea; m.p. 135°–137°C.

EXAMPLE 13

1-(4-Chlorophenyl)-3-butanimidoyl)urea

Following a procedure similar to that described in Example 1 but using 2.5 g. sodium in 150 ml. dry acetone, 14 g. butyramidine hydrochloride, and 16.8 g. 4-chlorophenyl isocyanate in 70 ml. dry acetone, there was obtained after recrystallization from ethyl alcohol 20.6 g. of the hydrochloride of 1-(4-chlorophenyl)-3-(butanimidoyl)urea; m.p. 206°–208°C.

EXAMPLE 14

1-(4-Chlorophenyl)-3-(heptanimidoyl)urea

Following a procedure similar to that described in Example 1 but using 3.9 g. sodium in 300 ml. dry acetone, 24.6 g. heptanamidine hydrochloride, and 23 g. 4-chlorophenyl isocyanate in 100 ml. dry acetone, there was obtained after recrystallization from acetonitrile 29.8 g. of the hydrochloride of 1-(4-chlorophenyl)-3-(heptanimidoyl)urea; m.p. 168°–169°C.

EXAMPLE 15

1-(3-Nitrophenyl)-3-(pentanimidoyl)urea

Following a procedure similar to that described in Example 1 but using 2.3 g. sodium in 150 ml. dry acetone, 13.6 g. valeramidine hydrochloride, and 16.4 g. 3-nitrophenyl isocyanate in 300 ml. benzene, there was obtained after recrystallization from ethyl alcohol-ether 11.6 g. of the hydrochloride of 1-(3-nitrophenyl)-3-(pentanimidoyl)urea; m.p. 161°–163°C.

EXAMPLE 16

1-(2-Nitrophenyl)-3-(pentanimidoyl)urea

Following a procedure similar to that described in Example 1 but using 2.3 g. sodium in 150 ml. dry acetone, 13.6 g. valeramidine hydrochloride, and 16.4 g. 2-nitrophenyl isocyanate in 300 ml. benzene, there was obtained after recrystallization from ethyl alcohol 9.1 g. of the hydrochloride of 1-(2-nitrophenyl)-3-(pentanimidoyl)urea; m.p. 130°–132°C.

EXAMPLE 17

1-[3-(Trifluoromethyl)phenyl]-3-(pentanimidoyl)urea

Following a procedure similar to that described in Example 1 but using 2.3 g. sodium in 250 ml. dry acetone, 13.6 g. valeramidine hydrochloride, and 18.7 g. 3-(trifluoromethyl)phenyl isocyanate in 100 ml. dry acetone, there was obtained after recrystallization from acetonitrile 17.9 g. of the hydrochloride of 1-[3-(trifluoromethyl)phenyl]-3-(pentanimidoyl)urea; m.p. 167°–169°C.

EXAMPLE 18

1-[2-(Benzyloxy)phenyl]-3-(pentanimidoyl)urea

Following a procedure similar to that described in Example 1 but using 2.9 g. sodium in 300 ml. dry acetone, 17.7 g. valeramidine hydrochloride, and 29.3 g. 2-(benzyloxy)phenyl isocyanate in 200 ml. dry acetone, there was obtained after recrystallization from isopropyl alcohol 33.9 g. of the hydrochloride of 1-[2-(benzyloxy)phenyl]-3-(pentanimidoyl)urea; m.p. 145°–147°C.

EXAMPLE 19

1-(2-Hydroxyphenyl)-3-(pentanimidoyl)urea

A suspension of 9.65 g. of the hydrochloride of 1-[2-benzyloxy)phenyl]-3-(pentanimidoyl)urea (see Example 18) in 20 ml. ice-cold water was treated with 5 ml. concentrated ammonium hydroxide solution, extracted with ether and the ethereal solution was dried over calcium sulfate and evaporated to dryness under reduced pressure. A solution of the residual free base in 80 ml. absolute ethyl alchol was hydrogenated over 1.2 g. palladium-charcoal at 82 pounds pressure at room temperature. When the required uptake of hydrogen was completed, the mixture was filtered and the filtrate was evaporated to dryness under reduced pressure. A solution of the residue in ether was chilled and treated with ethereal hydrogen chloride until acidic. The resulting solid was collected by filtration and recrystallized from ethyl alcohol-ether to give 4.5 g. of the hydrochloride of 1-(2-hydroxyphenyl)-3-(pentanimidoyl)urea; m.p. 173°–175°C.

EXAMPLE 20

1-(4-Bromophenyl)-3-(pentanimidoyl)urea

Following a procedure similar to that described in Example 1 but using 2.3 g. sodium in 300 ml. dry acetone, 13.6 g. valeramidine hydrochloride, and 19.8 g. 4-bromophenyl isocyanate, there was obtained after recrystallization from ethyl alcohol 21 g. of the hydrochloride of 1-(4-bromophenyl)-3-(pentanimidoyl)urea; m.p. 210°–212°C.

EXAMPLE 21

1-(4-Fluorophenyl)-3-pentanimidoyl)urea

Following a procedure similar to that described in Example 1 but using 8.4 g. sodium in 600 ml. dry acetone, 49.6 g. valeramidine hydrochloride, and 50 g. 4-fluorophenyl isocyanate in 150 ml. dry acetone, there was obtained after recrystallization from isopropyl alcohol 61.3 g. of the hydrochloride of 1-(4-fluorophenyl)-3-(pentanimidoyl)urea; m.p. 167°–172°C.

EXAMPLE 22

1-(4-Chlorophenyl)-3-(propanimidoyl)urea

To a stirred, cooled mixture of 10.8 g. sodium methoxide in 100 ml. dry benzene was added 21.6 g. propionamidine hydrochloride in one portion and stirring was continued for twenty minutes. To this mixture at room temperature was added a solution of 30.6 g. of 4-chlorophenyl isocyanate in 100 ml. benzene dropwise during 15 minutes and stirring was continued for 18 hours. The mixture was filtered and the filtrate was evaporated to dryness under reduced pressure. A solution of the resulting residue in either was chilled and treated with ethereal hydrogen chloride until acidic. The solid was collected by filtration to give after recrystallization from acetonitrile 22 g. of the hydrochloride of 1-(4-chlorophenyl)-3-(propanimidoyl)urea; m.p. 191°–192°C.

EXAMPLE 23

1-Phenyl-3-(heptanimidoyl)urea

To a stirred mixture, prepared by reacting 4.5 g. sodium with 350 ml. dry acetone at room temperature, was added 32.8 g. heptanamidine hydrochloride in one portion and stirring was continued for 20 minutes. To the resulting mixture was added dropwise, during 1½ hours, a solution of 23.8 g. phenyl isocyanate in 100 ml. dry acetone with stirring and external cooling in order to prevent the exothermic reaction from heating the mixture above room temperature. Stirring was continued at room temperature for 18 hours and the mixture was concentrated to dryness under pressure. The residue was taken up in ether and the sodium chloride was removed by filtration. The filtrate was chilled and treated with ethereal hydrogen chloride until acidic and the resulting solid was collected by filtration, washed with ether, and recrystallized from acetonitrile to give 25.3 g. 1-phenyl-3-(heptanimidoyl)urea hydrochloride; m.p. 151°–152°C.

Following a procedure similar to that described in Example 23 but substituting for heptanamidine hydrochloride an equivalent amount of the hydrochlorides of the following:
a. N-methylvaleramidine
b. N-isopropylvaleramidine
c. N-hexylvaleramidine
there can be obtained respectively the hydrochlorides of the following:
a. 1-(phenyl)-3-(N-methylheptanimidoyl)urea
b. 1-(phenyl)-3-(N-isopropylheptanimidoyl)urea
c. 1-(phenyl)-3-(N-hexylheptanimidoyl)urea.

Following a procedure similar to that described in Example 23 but substituting for heptanamidine hydrochloride an equivalent amount of the hydrochlorides of the following:
a. acetamidine
b. isobutyramidine
c. 3,7-dimethyloctanamidine
d. tridecanamidine
e. pentadecanamidine
there can be obtained respectively the hydrochlorides of the following:
a. 1-phenyl-3-(acetimidoyl)urea
b. 1-phenyl-3-(isobutyrimidoyl)urea
c. 1-phenyl-3-(3,7-dimethyloctanimidoyl)urea
d. 1-phenyl-3-(tridecanimidoyl)urea
e. 1-phenyl-3-(pentadecanimidoyl)urea.

EXAMPLE 24

1-Phenyl-3-(pentanimidoyl)urea

Following a procedure similar to that described in Example 23 but using 6.9 g. sodium in 300 ml. dry acetone, 41.1 g. valeramidine hydrochloride, and 35.7 g. phenyl isocyanate in 200 ml. dry acetone, there was obtained after recrystallization from ethyl alcohol 40.3 g. 1-phenyl-3-(pentanimidoyl)urea hydrochloride; m.p. 155.5°–156°C.

EXAMPLE 25

1-(4-Tolyl)-3-(pentanimidoyl)urea

Following a procedure similar to that described in Example 23 but using 2.3 g. sodium in 300 ml. dry acetone; 13.6 g. valeramidine hydrochloride and 13.3 g. 4-tolyl isocyanate in 100 ml. dry acetone, there was obtained after recrystallization from acetonitrile 10.6 g. 1-(4-tolyl)-3-(pentanimidoyl)urea hydrochloride; m.p. 159°–160°C.

Following the general procedure described hereinbefore for the preparation of phenyl isocyanates from the corresponding phenylamines and exemplified in Example 6B there can be obtained respectively from the following amines:
a. 4-hexylaniline
b. 2,3,4,5-tetramethylaniline
c. 2-ethyl-6-isopropylaniline
d. 4-tert-pentylaniline
the following isocyanates:
a. 4-hexylphenyl isocyanate
b. 2,3,4,5-tetramethylphenyl isocyanate
c. 2-ethyl-6-isopropylphenyl isocyanate
d. 4-tert-pentylphenyl isocyanate.

Following a procedure similar to that described in Example 23 but substituting for phenyl isocyanate an equivalent amount of the phenyl isocyanates listed from (a) to (d) inclusive above, there can be obtained respectively the hydrochlorides of the following:
a. 1-(4-hexylphenyl)-3-(heptanimidoyl)urea
b. 1-(2,3,4,5-tetramethylphenyl)-3-(heptanimidoyl)urea
c. 1-(2-ethyl-6-isopropylphenyl)-3-(heptanimidoyl)urea
d. 1-(4-tert-pentylphenyl)-3-(heptanimidoyl)urea.

The compounds listed below, in addition to their anti-hookworm activity, were also found to have anti-tapeworm activity against *Taenia pisiformis* and *Dipylidium caninum* when administered to such tapeworminfected dogs in the dose range of from 85 to 90 mg./kg. once daily for three consecutive days:

1-(4-Chlorophenyl)-3-(pentanimidoyl)urea (Example 1)

1-(2-Chlorophenyl)-3-(pentanimidoyl)urea (Example 5)

1-(4-Chlorophenyl)-3-(hexanimidoyl)urea (Example 8)

1-(2-Nitrophenyl)-3-(pentanimidoyl)urea (Example 16)

1-[3-(Trifluoromethyl)phenyl]-3-(pentanimidoyl)urea (Example 17)

1-[2-Benzyloxy)phenyl]-3-(pentanimidoyl)urea (Example 18)

1-(4-Bromophenyl)-3-(pentanimidoyl)urea (Example 20).

EXAMPLE 26

1-Phenyl-3-(acetimidoyl)urea

Following a procedure similar to that described in Example 23 but using 4.6 g. sodium in 500 ml. dry acetone, 18.8 g. acetamidine hydrochloride and 23.8 g. phenyl isocyanate in 100 ml. dry acetone, there was obtained after recrystallization from isopropyl alcohol 27.1 g. 1-phenyl-3-(acetimidoyl)urea hydrochloride; m.p. 204°–206°C.

EXAMPLE 27

1-(4-Tolyl)-3-(acetimidoyl)urea

Following a procedure similar to that described in Example 23 but using 4.6 g. sodium in 500 ml. dry acetone, 18.8 g. acetamidine hydrochloride and 26.6 g. 4-tolyl isocyanate in 120 ml. of dry acetone, there was obtained after recrystallization from isopropyl alcohol 27.1 g. 1-(4-tolyl)-3-(acetimidoyl) urea hydrochloride; m.p. 210°–212°C.

EXAMPLE 28

1-(3-Chloro-4-cyanophenyl)-3-(propanimidoyl)urea

A. Following a procedure similar to that described in Example 1 but using 1.22 g. sodium in 150 ml. dry acetone, 6.5 g. propionamidine hydrochloride and 9.5 g. 3-chloro-4-cyanophenyl isocyanate in 150 ml. dry acetone there was obtained, after concentration of the reaction mixture to dryness under reduced pressure, a residue which was partitioned between water and ether. The ether extract was evaporated to dryness to give, after recrystallization from isopropyl alcohol 5.1 g. 1-(3-chloro-4-cyanophenyl)-3-(propanimidoyl)urea; m.p. 164°–166°C.

B. 3-Chloro-4-cyanophenyl isocyanate hydrochloride, m.p. 89–91°C., was obtained by a procedure similar to that described hereinbefore (Example 6E), from 4-amino-2-chlorobenzonitrile hydrochloride.

C. 4-Amino-2-chlorobenzonitrile hydrochloride was prepared as follows:

A suspension of 25 g. 2-chloro-4-nitrobenzonitrile hydrochloride and 3 g. granular tin in 147 ml. concentrated hydrochloric acid was warmed to 50°C. and when vigorous hydrogen evolution started 56 g. tin was added in 3 to 5 g. portions with cooling to maintain reaction at 90 to 100°C. The mixture was heated at reflux for 45 minutes, the unreacted tin was separated by decantation, and the resulting solution was concentrated under reduced pressure till about 80 ml. of water was collected, the residual solution was made strongly alkaline with 130 ml. 35% sodium hydroxide solution, and the solids were collected by filtration, dissolved in ether and treated with ethereal hydrogen chloride to give, on filtration, 4-amino-2-chlorobenzonitrile hydrochloride; m.p. 170°–180°C.

D. 4-Nitro-2-chlorobenzonitrile was prepared as follows:

A mixture of 18.2 g. 2-chloro-4-nitrobenzamide, 20.9 g. phosphorus pentachloride and 20 ml. carbon tetrachloride was slowly heated till vigorous gas evolution ensued (40°C.). Heat was removed till gas evolution became gentle and the solution was heated at reflux for 20 minutes. The solution was evaporated to dryness and the resulting residue was heated till the internal temperature reached 135°C. when vigorous bubbling began. Heat was removed till bubbling became gentle and the reaction mixture was heated at 140°–145°C. (internal) for thirty minutes. The mixture was distilled under pressure to remove phosphorus oxychloride and the resulting residue was crystallized from ethyl alcohol to give 9.6 g. 4-nitro-2-chlorobenzonitrile; m.p. 80°–81°C.

EXAMPLE 29

1-(3-Chloro-4-cyanophenyl)-3-(acetimidoyl)urea

Following a procedure similar to that described in Example 1 but using 2.06 g. sodium in 250 ml. dry acetone, 9.2 g. acetamidine hydrochloride and 16 g. 3-chloro-4-cyanophenyl isocyanate in 250 ml. dry acetone, there was obtained after filtration of the reaction mixture a solid which on washing with water and recrystallization from methyl alcohol gave 1-(3-chloro-4-cyanophenyl)3-(acetimidoyl)urea; m.p.182°–183°C.

EXAMPLE 30

1-(3-Chloro-4-cyanophenyl)-3-(pentanimidoyl)urea

Following a procedure similar to that in Example 1 but using 2.38 g. sodium in 275 ml. dry acetone, 14.9 g. valeramidine hydrochloride and 18.5 g. 3-chloro-4-cyanophenyl isocyanate there was obtained 24.5 g. 1-(3-chloro4-cyanophenyl)-3-(pentanimidoyl)urea hydrochloride; m.p. 198°–201°C.

A solution of 1 g. of the hydrochloride in 75 ml. ether was treated with 0.33 g. triethylamine in 10 ml. ether. The cooled mixture was filtered and the filtrate was evaporated to dryness under reduced pressure to give, after recrystallization from acetonitrile, 1-(3-chloro-4-cyanophenyl)-3-(pentanimidoyl)urea; m.p. 154°–156°C.

EXAMPLE 31

1-Methyl-1-phenyl-3-(pentanimidoyl)urea

A. To a stirred mixture, prepared by reacting 2.3 g. sodium with 400 ml. dry tert butyl alcohol, was added 13.6 g. valeramidine hydrochloride, 11 ml. triethylamine and 13 g. N-phenyl-N-methylcarbamyl chloride in 300 ml. dry tert-butyl alcohol. Stirring was continued four hours, the mixture was filtered and the filtrate was evaporated to dryness under reduced pressure to give on recrystallization from methyl alcohol 4 g. 1-methyl-1-phenyl-3-(pentanimidoyl)urea; m.p. 82°–84°C.

The hydrochloride salt, prepared by treatment of the urea with ethereal hydrogen chloride, was treated in water with an equimolar quantity of disodium 4,4'-methylenebis-(3-hydroxy-2-naphthonate (disodium pamoate) to give after filtration and recrystallization of the resulting solids from isopropyl alcohol, 1-methyl-1-phenyl-3-(pentanimidoyl)urea pamoate; m.p. 201°–202°C.

B. N-Phenyl-N-methylcarbamyl chloride was prepared as follows:

To a stirred solution of 29.4 g. phosgene in 350 ml. dry chloroform at 5°C. was added a solution of 32.1 g. N-methylaniline and 23.7 g. dry pyridine in 80 ml. dry chloroform dropwise during 45 minutes and the resulting solution was allowed to stand at 5°C. for 3 hours. The solution was evaporated to dryness under reduced pressure and the resulting residue was dissolved in ether. The ethereal solution was heated with magnesium sulfate, filtered, the filtrate was evaporated to dryness under reduced pressure and the resulting solid was slurried in n-hexane and filtered to give 31.5 g. N-phenyl- N-methylcarbamyl chloride; m.p. 90°–91°C.

EXAMPLE 32

1-Methyl-1-(4-chlorophenyl)-3-(pentanimidoyl)urea

A. Following a procedure similar to that described in Example 31A but using 2.3 g. sodium in 400 ml. dry tert-butyl alcohol, 13.6 g. valeramidine hydrochloride, 10 ml. triethylamine and 20 g. N-(4-chlorophenyl)-N-methylcarbamyl chloride in 300 ml. dry tert-butyl alcohol there was obtained after conversion of the crude product to the pamoate salt by the procedure described in Example 31A followed by recrystallization from isopropyl alcohol, 7 g. 1-methyl-1-(4-chlorophenyl)-3-(pentanimidoyl)urea pamoate; m.p. 180°–182°C.

B. N-(4-Chlorophenyl)-N-methylcarbamyl chloride; m.p. 59°–61°C., was prepared from N-methyl-p-chloroaniline by a procedure similar to that described in Example 31B.

By following a procedure similar to that described in Example 31B but substituting for N-methylaniline an equivalent amount of the following:
  a. N-hexylaniline
  b. N-isopropylaniline
there can be obtained respectively:
  a. N-Phenyl-N-hexylcarbamyl chloride
  b. N-Phenyl-N-isopropylcarbamyl chloride.

By following a procedure similar to that described in Example 31A but substituting for N-phenyl-N-methylcarbamyl chloride an equivalent amount of the carbamyl chlorides (a) and (b) above there can be obtained respectively:
  a. 1-Hexyl-1-phenyl-3-(pentanimidoyl)urea
  b. 1-Isopropyl-1-phenyl-3-(pentanimidoyl)urea

EXAMPLE 33

1-(4-Chlorophenyl)-3-[4-(dimethylamino)-butanimidoyl]urea

A. To a stirred mixture, prepared by reacting 1.35 g. sodium with 50 ml. dry acetone, was added 4.9 g. 4-(dimethylamino)-butyramidine dihydrochloride in one portion and stirring was continued for 30 minutes. To the resulting mixture cooled to 5°C. was added, dropwise during 30 minutes, a solution of 4.52 g. 4-chlorophenyl isocyanate in 50 ml. dry acetone. Stirring was continued at room temperature for 18 hours and the mixture was concentrated to dryness under reduced pressure. A stirred solution of the residue in 100 ml. isopropyl alcohol, cooled to 5°C., was treated with ethereal hydrogen chloride until the mixture was acidic. The solid was collected by filtration and crystallized from isopropyl alcohol to give 6 g. 1-(4-chlorophenyl)-3-[4-(dimethylamino)butanimidoyl]urea dihydrochloride; m.p. 197°–199°C.

B. 4-(Dimethylamino)butyramidine dihydrochloride was prepared as follows:

To a solution, prepared by saturating 200 ml. methyl alcohol at 5°C. with hydrogen chloride, was added dropwise during 20 minutes, with continued cooling, 10 g. 4-(dimethylamino)butyronitrile and stirring at 5°C. was continued for 45 minutes. The resulting oily layer was separated from the mixture, washed with ether, dissolved in 50 ml. absolute ethyl alcohol. The resulting solution was chilled, ammonia was added till the solution was basic, and the solution was allowed to stand for 12 hours at 5°C. The mixture was filtered and the filtrate concentrated to 20 ml., treated with ether till turbid, and refiltered. The filtrate was then treated with ethereal hydrogen chloride till acidic and the solid was collected by filtration and recrystallization from isopropyl alcohol to give 4.9 g. 4-(dimethylamino)-butyramidine dihydrochloride; m.p. 184°–186°C.

C. Compounds having the formula $R_1R_2N-(CH_2)_n-C\equiv N$ are prepared by a procedure exemplified as follows for the preparation of 5-(dimethylamino)-valeronitrile:

A solution of 52.5 g. sodium iodide and 50 g. 5-bromovaleronitrile in 175 ml. acetone was stirred at room temperature for 18 hours and then heated under reflux for 2 hours. The mixture was filtered and the filtrate was evaporated to dryness under reduced pressure. The residue was dissolved in ether and the solution was washed with water, dried, and evaporated to dryness. The resulting oil was added to a solution of 53 g. dimethylamine in 150 ml. benzene with cooling. The solution was stirred 18 hours at room temperature and then heated under reflux for 2 hours. The cooled mixture was filtered and the filtrate was treated with 35 ml. concentrated hydrochloric acid. The aqueous layer was separated, treated with a solution of 20 g. sodium hydroxide in 40 ml. water, and extracted with ether. The ether extract was dried and evaporated to dryness to give, after distillation under reduced pressure 31.2 g. 5-(dimethylamino) valeronitrile, b.p. 78°–80°C. (9 mm.), $n^{25}D$ 1.4318.

Following procedures described in Example 33B. and Example 33C there was obtained from the following:
  a. 6-bromohexanenitrile
  b. 11-bromoundecanenitrile
  c. 5-bromovaleronitrile
the dihydrochlorides of the following:
  a. 6-(dimethylamino)hexanamidine
  b. 11-(dimethylamino)undecanamidine
  c. 5-(dimethylamino)valeramidine Following the procedure described in Example 33A but substituting for 4-(dimethylamino)butyramidine hydrochloride equivalent amounts of the dihydrochlorides of the amidines listed from (a) to (c) inclusive above there are obtained respectively the dihydrochlorides of the following:
  a. 1-(4-Chlorophenyl)-3-[6-(dimethylamino)hexanimidoyl]urea
  b. 1-(4-Chlorophenyl)-3-[11-(dimethylamino)undecanimodoyl]urea
  c. 1-(4-Chlorophenyl)-3-[5-(dimethylamino)pentanimidoyl]urea Following a procedure similar to that described in Example 33C but substituting an equivalent amount of 4-bromobutyronitrile for 5-bromovaleronitrile and for dimethylamine equivalent amounts of the following amines
  a. diethylamine
  b. di-n-hexylamine
  c. dibenzylamine d. N-methyl-n-hexylamine
e. morpholine
f. thiomorpholine
g. piperidine
h. pyrrolidine
i. piperazine
j. N-methylpiperazine
k. N-phenylpiperazine there can be obtained respectively:
a. 4-(diethylamino)butyronitrile
b. 4-(di-n-hexylamino)butyronitrile
c. 4-(dibenzylamino)butyronitrile
d. 4-(N-methyl-n-hexylamino)butyronitrile
e. 4-(1-morpholinyl)butyronitrile
f. 4-(1-thiomorpholinyl)butyronitrile
g. 4-(1-piperidinyl)butyronitrile
h. 4-(1-pyrrolidinyl)butyronitrile
i. 4-(1-piperazinyl)butyronitrile
j. 4-(4-methyl-1-piperazinyl)butyronitrile
k. 4-(4-phenyl-1-piperazinyl)butyronitrile Following a procedure similar to that described in Example 33B and substituting for 4-(dimethyl)-butyronitrile equivalent amounts of the butyronitriles listed from (a) to (h) inclusive above, there are obtained respectively the dihydrochlorides of:
a. 4-(diethylamino)butyramidine
b. 4-(di-n-hexylamino)butyramidine
c. 4-(dibenzylamino)butyramidine
d. 4-(N-methyl-n-hexylamino)butyramidine
e. 4-(1-morpholinyl)butyramidine
f. 4-(1-thiomorpholinyl)butyramidine
g. 4-(1-piperidinyl)butyramidine
h. 4-(1-pyrrolidinyl)butyramidine Following a procedure similar to that described in Example 33B and substituting for 4-(dimethyl)-butyronitrile equivalent amounts of the butyronitriles listed from (i) to (k) inclusive above and substituting equivalent amounts of methylamine, isopropylamine and hexylamine respectively for ammonia there are obtained the dihydrochlorides of:
i. 4-(1-piperazinyl)-N-methylbutyramidine
j. 4-(4-methyl-1-piperazinyl)-N-isopropylbutyramidine
k. 4-(4-phenyl-1-piperazinyl)-N-hexylbutyramidine Following a procedure similar to that described in Example 33A but substituting for 4-(dimethylamino) butyramidine dihydrochloride equivalent amounts of the dihydrochlorides of the amidines listed from (a) to (k) above and substituting respectively for 4-chlorophenyl isocyanate equivalent amounts of the following isocyanates:
a. phenyl isocyanate
b. 4-methoxyphenyl isocyanate
c. 4-nitrophenyl isocyanate
d. 3-(trifluoromethyl)phenyl isocyanate
e. 2-benzyloxyphenyl isocyanate
f. 4-tolyl isocyanate
g. 4-fluorophenyl isocyanate
h. 4-hexyloxyphenyl isocyanate
i. 4-(5-phenylpentyloxy)phenyl isocyanate
j. 4-acetamidophenyl isocyanate
k. 4-diethylaminophenyl isocyanate and by following a procedure similar to that described in Example 33A but substituting for 4-chlorophenyl isocyanate equivalent amounts of the following isocyanates:
l. 3-methylsulfinylphenyl isocyanates
m. 4-hexylsulfonylphenyl isocyanate
n. 4-methylsulfonylphenyl isocyanate
o. 3-hexylthiophenyl isocyanate
p. pentachlorophenyl isocyanate
q. 4-bromo-2-methylphenyl isocyanate
r. 4-acetoxyphenyl isocyanate there are obtained respectively the dihydrochlorides of
a. 1-phenyl-3-(4-diethylaminobutyrimidoyl)urea
b. 1-(4-methoxyphenyl)-3-(4-di-n-hexylaminobutyrimidoyl) urea
c. 1-(4-nitrophenyl)-3-(4-dibenzylaminobutyrimidoyl)urea
d. 1-[3-(trifluoromethyl)phenyl]-3-[4-(N-methyl-n-hexylamino)butyrimidoyl]urea
e. 1-(2-benzyloxyphenyl)-3-[4-(1-morpholinyl)-butyrimidoyl]urea
f. 1-(4-tolyl)-3-[4-(1-thiomorpholinyl)butyrimidoyl]urea
g. 1-(4-fluorophenyl)-3-[4-(1-piperidinyl)-butyrimidoyl]urea
h. 1-(4-hexyloxyphenyl)-3-[4-(1pyrrolidinyl)-butyrimidoyl]urea
i. 1-[4-(5-phenylpentyloxy)phenyl]-3-[4-(1-piperazinyl)-N-methlybutyrimidoyl]urea
j. 1-(4-acetamidophenyl)-3-[4-(4-methyl-1-piperazinyl)-N-isopropyl butyrimidoyl]urea
k. 1-(4-diethylaminophenyl)-3-[4-(4-phenyl-1-piperazinyl)-N-hexylbutyrimidoyl]urea
l. 1-(3-methylsulfinylphenyl)-3-[4-(dimethylamino)-butyrimidoyl]urea
m. 1-(4-hexylsulfonylphenyl)-3-[4-(dimethylamino)-butyrimidoyl]urea
n. 1-(4-methylsulfonyl)-3-[4-(dimethylamino)-butyrimidoyl]urea
o. 1-(3-hexylthiophenyl)-3-[4-(dimethylamino)-butyrimidoyl]urea
p. 1-(pentachlorophenyl)-3-[4-(dimethylamino)-butyrimidoyl]urea
q. 1-(4-bromo-2-methylphenyl)-3-[4-(dimethylamino)butyrimidoyl]urea
r. 1-(4-acetoxyphenyl)-3-[4-(dimethylamino)-butyrimidoyl]urea

EXAMPLE 34

1-(4-Chlorophenyl)-3-(pentanimidoyl)-2thiourea

A stirred mixture, prepared by reacting 4.6 g. sodium with 300 ml. dry acetone at room temperature was cooled to 5°C. and 27.3 g. valeramidine hydrochloride was added in one portion. After 20 minutes there was added dropwise during thirty minutes, a solution of 33.8 g. 4-chlorophenyl isothiocyanate in 200 ml. dry acetone while the temperature was maintained at 5° to 10°C. The mixture was stirred for 18 hours at room temperature, filtered and the filtrate was evaporated to dryness under reduced pressure. A solution of the residue in 300 ml. ether was chilled and treated with ethereal hydrogen chloride until acidic and the resulting solid was filtered to give, after recrystallization from acetonitrile 51.1 g. 1-(4-chlorophenyl)-3-(pentanimidoyl)-2-thiourea hydrochloride; m.p. 164°–166°C.

EXAMPLE 35

1-(4-Chlorophenyl)-3-(heptanimidoyl)-2-thiourea

Following a procedure similar to that described in Example 34 but substituting for valeramidine hydrochloride an equivalent amount of heptanamidine hydrochloride there was obtained after filtration of the reaction mixture and evaporation to dryness of the resulting filtrate a solid which was recrystallized from benzene-(n-hexane) to give 9.1 g. 1-(4-chlorophenyl)-3-heptanimidoyl)-2-thiourea; m.p. 112°–113°C.

By following a procedure similar to that described in Example 34 but substituting for valeramidine hydrochloride an equivalent amount of the hydrochlorides of:
a. acetamidine
b. isobutyramidine
c. pentadecanamidine there are obtained respectively the hydrochlorides of:
a. 1-(4-chlorophenyl)-3-(acetamidoyl)-2-thiourea
b. 1-(4-chlorophenyl)-3-(isobutyrimidoyl)-2-thiourea
c. 1-(4-chlorophenyl)-3-(pentadecanimidoyl)-2-thiourea By following a procedure similar to that described in Example 34 but substituting for 4-chlorophenyl isothiocyanate the following isothiocyanates:
a. 4-fluorophenyl isothiocyanate
b. 4-methoxyphenyl isothiocyanate
c. 2,4-dinitrophenyl isothiocyanate
d. 4-dimethylaminophenyl isothiocyanate
e. 4-hexyloxyphenyl isothiocyanate
f. 3,4-dichlorophenyl isothiocyanate
g. 3-acetamidophenyl isothiocyanate
h. 4-acetoxyphenyl isothiocyanate
i. 2-isopropoxyphenyl isothiocyanate
j. 4-trifluoromethoxyphenyl isothiocyanate
k. 4-trifluoromethylphenyl isothiocyanate there are obtained respectively the hydrochlorides of:
a. 1-(4-fluorophenyl)-3-(pentanimidoyl)-2-thiourea
b. 1-(4-methoxyphenyl)-3-(pentanimidoyl)-2-thiourea
c. 1-(2,4-dinitrophenyl)-3-(pentanimidoyl)-2-thiourea
d. 1-(4-dimethylaminophenyl)-3-(pentanimidoyl)-2-thiourea
e. 1-(4-hexyloxyphenyl)-3-(pentanimidoyl)-2-thiourea
f. 1-(3,4-dichlorophenyl)-3-(pentanimidoyl)-2-thiourea
g. 1-(3-acetamidophenyl)-3-(pentanimidoyl)-2-thiourea
h. 1-(4-acetoxyphenyl)-3-(pentanimidoyl)-2-thiourea
i. 1-(2-isopropoxyphenyl)-3-(pentanimidoyl)-2-thiourea
j. 1-(4-trifluoromethoxyphenyl)-3-(pentanimidoyl)-2-thiourea
k. 1-(4-trifluoromethylphenyl)-3-(pentanimidoyl)-2-thiourea

EXAMPLE 36

1-(4-Nitrophenyl)-3-benzimidoylurea

Following a procedure similar to that described in Example 1 but using 2.3 g. sodium in 150 ml. dry acetone, concentrating the mixture to .15 ml. and adding 15.6 g. benzamidine hydrochloride in 150 ml. benzene and 16.4 g. 4-nitrophenyl isocyanate in 250 ml. benzene there was obtained, after recrystallization from benzene, 13 g. 1-(4-nitrophenyl)-3-benzimidoylurea; m.p. 188°–191°C.

EXAMPLE 37

1-(2-Nitrophenyl)-3-benzimidoylurea

To a solution of 28.9 g. benzamidine hydrochloride dihydrate in 50 ml. water was added, with cooling, 8 g. sodium hydroxide in 100 ml. water. The solution was extracted with ether and the extract was dried and evaporated to dryness under reduced pressure. To the resulting residue, dissolved in 150 ml. p-dioxane, was added 16.4 g. 2-nitrophenyl isocyanate in 50 ml. p-dioxane during one-half hour. After standing 18 hours, the solution was evaporated to dryness under reduced pressure to give, after recrystallization from benzene-(n-hexane) 14.4 g. 1-(2-nitrophenyl)-3-benzylimidoylurea; m.p. 143.6°–146.0°C.

EXAMPLE 38

1-(4-Chlorophenyl)-3-(5-nitro-2-furylcarbimidoyl)urea

To a suspension of 7.6 g. 5-nitrofuramidine hydrochloride in 100 ml. chloroform was added 4.05 g. triethylamine, the suspension was stirred 15 minutes, and then a solution of 6.12 g. 4-chlorophenyl isocyanate in 50 ml. chloroform was added dropwise. The mixture was stirred 18 hours, chilled and filtered to give, after recrystallization from ethyl alcohol, 8.6 g. 1-(4-chlorophenyl)-3-(5-nitro-2-furylcarbimidoyl)urea; m.p. 189°C. (dec.).

EXAMPLE 39

1-Cyclohexyl-3-(pentanimidoyl)urea

Following a procedure similar to that described in Example 23 but using 8.4 g. sodium in 1100 ml. dry acetone, 50 g. valeramidine hydrochloride, and 46.4 g. cyclohexyl isocyanate in 300 ml. dry acetone there was obtained, after recrystallization from isopropyl alcohol 58.4 g. 1-cyclohexyl-3-(pentanimidoyl)urea hydrochloride; m.p. 146°–148°C.

EXAMPLE 40

1-Butyl-3-(benzimidoyl)urea

Following a procedure similar to that described in Example 23 but using 7.7 g. sodium in 1100 ml. dry sodium, 52.4 g. benzamidine hydrochloride, and 33.1 g. butylisocyanate in 400 ml. dry acetone there was obtained, after recrystallization from ethyl acetate, 62.2 g. 1-butyl-3-(benzimidoyl)urea hydrochloride; m.p. 139°–141°C.

EXAMPLE 41

1-(2-Thienyl)-3-(pentanimidoyl)urea

Following a procedure similar to that described in Example 38 but using 21.8 g. valeramidine hydrochloride in 40 ml. dry acetone, 1162 g. triethylamine, and 2 g. 2-thienyl isocyanate in 40 ml. dry acetone there was obtained, after extraction of the reaction mixture with ether-water and treatment of the dry ethereal extract with ethereal hydrogen chloride, filtration and recrystallization from isopropyl alcohol 2g. 1-(2-thienyl)-3-(pentanimidoyl)urea hydrochloride; m.p. 174°–176°C.

By following a procedure similar to that described in Example 33A but substituting for the dihydrochloride of 4-(dimethylamino)butyramidine and for 4-chlorophenyl isocyanate respectively an equivalent amount of the dihydrochlorides of the amidines and the phenyl isocyanates listed below:

a. 13-(dimethylamino)tridecanamidine and 2-chloro-5-hexylphenyl isocyanate
b. 3-(dimethylamino)butyramidine and 4-bromo-2,6-diiodophenyl isocyanate
c. 2-(dimethylamino)acetamidine and 4-bromo-3-tert-butylphenyl isocyanate there are obtained respectively the dihydrochlorides of:
- a. 1-(2-chloro-5-hexylphenyl)-3-[13-(dimethylamino)tridecanimidoyl]urea
- b. 1-(4-bromo-2,6-diiodophenyl)-3-[3-(dimethylamino)butyrimidoyl]urea
- c. 1-(4-bromo-3-tert-butylphenyl)-3-[2-(dimethylamino)acetimidoyl]urea The phenyl isocyanates listed from a to c inclusive above are prepared from the corresponding 2-chloro-5-hexylaniline, 4-bromo-2,6-diiodoaniline and 4-bromo-3-tert-butylaniline respectively by following a procedure similar to that described in Example 6B.

By following procedures similar to those described in Examples 37 and 38 but substituting for 2-nitrophenyl isocyanate and 4-chlorophenyl isocyanate respectively an equivalent amount of the following isocyanates:
a. methyl isocyanate
b. isopropyl isocyanate
c. n-pentadecyl isocyanate there are obtained respectively the following imidoylureas:
- a. 1-methyl-3-benzimidoylurea and 1-methyl-3-(5-nitro-2-furylcarbimidoyl)urea
- b. 1-isopropyl-3-benzimidoylurea and 1-isopropyl-3-(5-nitro-2-furylcarbimidoyl)urea
- c. 1-(n-pentadecyl)-3-benzimidoylurea and 1-(n-pentadecyl)-3-(5-nitro-2-furylcarbimidoyl)urea By following a procedure similar to that described in Example 38 but substituting for 4-chlorophenyl isocyanate an equivalent amount of the following isocyanates:
a. 3,4-dichlorophenyl isocyanate
b. 2-bromo-4,6-difluorophenyl isocyanate
c. 4-bromo-2,6-diiodophenyl isocyanate
d. pentachlorophenyl isocyanate there are obtained respectively:
- a. 1-(3,4-dichlorophenyl)-3-(5-nitro-2-furylcarbimidoyl)urea
- b. 1-(2-bromo-4,6-difluorophenyl)-3-(5-nitro-2-furylcarbimidoyl)urea
- c. 1-(4-bromo-2,6-diiodophenyl)-3-(5-nitro-2-furylcarbimidoyl)urea
- d. 1-(pentachlorophenyl)-3-(5-nitro-2-furylcarbimidoyl)urea By following a procedure similar to that described in Example 38 but substituting for 4-chlorophenyl isocyanate an equivalent amount of the following isocyanates:
a. 2-nitrophenyl isocyanate
b. 4-nitrophenyl isocyanate there are obtained respectively the following:
- a. 1-(2-nitrophenyl)-3-(5-nitro-2-furylcarbimidoyl)urea
- b. 1-(4-nitrophenyl)-3-(5-nitro-2-furylcarbimidoyl)urea By following procedures similar to those described in Examples 39 and 41 but substituting for pentanamidine hydrochloride in each case an equivalent amount of the hydrochlorides of the following amidines:
a. acetamidine
b. 3,7-dimethyloctanamidine
c. pentadecanamidine there are obtained respectively the hydrochlorides of the following:
- a. 1-cyclohexyl-3-(acetimidoyl)urea and 1-(2-thienyl)-3-(acetimidoyl)urea
- b. 1-cyclohexyl-3-3,7dimethyloctanimidoyl)urea and 1-(2-thienyl)-3-(3,7-dimethyloctanimidoyl)urea
- c. 1-cyclohexyl-3-(pentadecanimidoyl)urea and 1-(2-thienyl)-3-(pentadecanimidoyl)urea

EXAMPLE 42

1-(4-Bromophenyl)-3-(heptanimidoyl)-2-thiourea

Following a procedure similar to that described in Example 34 and using 3.4 g. sodium in 300 ml. dry acetone, 24.7 g. heptanamidine hydrochloride, and 32.1 g. 4-bromophenyl isothiocyanate in 100 ml. acetone there was obtained 48.7 g. 1-(4-bromophenyl)-3-(heptanimidoyl)-2-thiourea hydrochloride; m.p. 171°–174°C.

An aqueous suspension of the above hydrochloride salt was treated with an excess of 1N-sodium hydroxide solution and then extracted with ether. The ether extracts were dried and evaporated to dryness under reduced pressure to yield 1-(4-bromophenyl)-3-(heptanimidoyl)-2-thiourea; m.p. 112°–113°C. (from benzene-n-pentane).

The 4-bromophenyl isothiocyanate was prepared by the following procedure:

To a stirred cooled mixture of 28 g. calcium carbonate in 150 ml. each of water and ethylenedichloride was added dropwise simultaneously but separately, a solution of 50 g. 4-bromoaniline in 150 ml. ethylenedichloride and 34.5 g. thiophosgene in 150 ml. ethylenedichloride at a rate which maintained thiophosgene in slight excess over 4-bromoaniline in the reaction mixture while the temperature was maintained at 12°–15°C. When the addition was completed stirring was continued at room temperature for four hours. The organic layer was separated, washed with 5% hydrochloric acid and water, dried and evaporated to dryness. The residue was distilled under reduced pressure to give 55 g. 4-bromophenyl isothiocyanate, b.p. 142°–144°C./14 mm., m.p. 61°–62°C.

The phenyl isothiocyanates used as starting materials for the preparation of the thioureas of this invention were prepared from the corresponding known anilines following a procedure similar to that described above for the preparation of 4-bromophenyl isothiocyanate.

EXAMPLE 43

1-(4-Methoxyphenyl-3-(heptanimidoyl)-2-thiourea

Following a procedure similar to that described in Example 42 but substituting for 4-bromophenyl isothiocyanate an equivalent amount of 4-methoxyphenyl isothiocyanate (b.p. 140°–145°C./14–17 mm.; prepared frm 4-methoxyaniline) there was obtained 1-(4-methoxyphenyl)-3-(heptanimidoyl)-2-thiourea, m.p. 70°–72°C. (from benzene-n-pentane); hydrochloride (27 g.), m.p. 163°–166°C.

EXAMPLE 44

1-(4-Chlorophenyl)-3-(octanimidoyl)-2-thiourea

Following a procedure similar to that described in Example 42 but using 2 g. sodium in 250 ml. dry acetone, 15.7 g. octanimidine hydrochloride, and 15 g. 4-chlorophenyl isothiocyanate (m.p. 44°–45°C.; prepared from 4-chloroaniline) in 70 ml. dry acetone there was obtained 1-(4-chlorophenyl)-3-(octanimidoyl)-2-thiourea, m.p. 98°–99°C. (from benzene-n-pentane);

hydrochloride (18.7 g.), m.p. 155°–157°C. (from acetonitrile).

EXAMPLE 45

1-(4-Chlorophenyl)-3-(hexanimidoyl)-2-thiourea

Following a procedure similar to that described in Example 42 but using 3.4 g. sodium in 300 ml. dry acetone, 22.5 g. hexanamidine hydrochloride, and 25.9 g. 4-chlorophenyl isothiocyanate in 150 ml. dry acetone there was obtained 1-(4-chlorophenyl)-3-(hexanimidoyl)-2-thiourea, m.p. 100°–102°C. (from benzene-n-pentane); hydrochloride (21 g.), m.p. 175°C. (from acetonitrile).

EXAMPLE 46

1-(4-Fluorophenyl)-3-(heptanimidoyl)-2-thiourea

Following a procedure similar to that described in Example 42 but using 1.6 g. sodium in 200 ml. dry acetone, 12.3 g. heptanamidine hydrochloride, and 11.6 g. 4-fluorophenyl isothiocyanate (b.p. 48°C./0.025 mm.; prepared from 4-fluoroaniline) in 50 ml. dry acetone there was obtained 1-(4-fluorophenyl)-3-(heptanimidoyl)-2-thiourea, m.p. 75°–76°C. (from benzene-n-pentane); hydrochloride (17.1 g.), m.p. 155°C. (from acetonitrile).

EXAMPLE 47

1-(4-Nitrophenyl)-3-(heptanimidoyl)-2-thiourea

Following a procedure similar to that described in Example 42 but using 34 g. sodium in 300 ml. dry acetone, 24.7 g. heptanamidine hydrochloride, and 27 g. 4-nitrophenyl isothiocyanate in 250 ml. acetone there was obtained 1-(4-nitrophenyl)-3-(heptanimidoyl)-2-thiourea, m.p. 89°–90°C. (from benzene-n-pentane); hydrochloride (33.4 g.), m.p. 150°–151°C. (from acetonitrile).

1-(4-Aminophenyl)-3-(heptanimidoyl)-2-thiourea can be obtained from 1-(4-nitrophenyl)-3-(heptanimidoyl)-2-thiourea by hydrogenation in absolute alcohol over Raney nickel at 400 pounds pressure at room temperature following a procedure similar to tht described in Example 10.

EXAMPLE 48

1-(3,4-Dichlorophenyl)-3-(heptanimidoyl)-2-thiourea

Following a procedure similar to that described in Example 42 but using 2.3 g. sodium in 250 ml. dry acetone, 16.4 g. heptanamidine hydrochloride, and 20.4 g. 3,4-dichlorophenyl isothiocyanate (b.p. 149–152/15–16 mm.) in 150 ml. dry acetone there was obtained 1-(3,4-dichlorophenyl)-3-(heptanimidoyl)-2-thiourea, m.p. 89°–90°C. (from benzene-n-pentane); hydrochloride (27 g.), m.p. 158°–160°C. (from acetonitrile).

EXAMPLE 49

1-(2,4-Dibromophenyl)-3-(heptanimidoyl)-2-thiourea

Following a procedure similar to that described in Example 42 but using 2.3 g. sodium in 300 ml. dry acetone, 16.5 g. heptanamidine hydrochloride, and 29.3 g. 2,4-dibromophenyl isothiocyanate (m.p. 68°–70°C.; prepared from 2,4-dibromoaniline) in 100 ml. dry acetone there was obtained 1-(2,4-dibromophenyl)-3-(heptanimidoyl)-2-thiourea, m.p. 86°–88°C. (from benzene-n-hexane); hydrochloride (14 g.), m.p. 164°–165°C. (from acetonitrile).

EXAMPLE 50

1-(4-Chloro-3-nitrophenyl)-3-(heptanimidoyl)-2-thiourea

Following a procedure similar to that described in Example 42 but using 2.3 g. sodium in 300 ml. dry acetone, 16.4 g. heptanamidine hydrochloride, and 21.4 g. 4-chloro-3-nitrophenyl isothiocyanate (m.p. 54°–56°C., prepared from 4-chloro-3-nitroaniline) in 100 ml. dry acetone there was obtained 1-(4-chloro-3-nitrophenyl)-3-(heptanimidoyl)-2-thiourea, m.p. 92°–94°C. (from benzene-n-pentane); hydrochloride (22.5 g.), m.p. 138°–140°C. (from acetonitrile).

EXAMPLE 51

1-(4-Chlorophenyl)-3-(nonanimidoyl)-2-thiourea

Following a procedure similar to that described in Example 42 but using 1.9 g. sodium in 200 ml. dry acetone, 16 g. nonanamidine hydrochloride, and 14.2 g. 4-chlorophenyl isothiocyanate in 100 ml. dry acetone there was obtained 1-(4-chlorophenyl)-3-(nonanimidoyl)-2-thiourea, m.p. 102°–103°C. (from benzene-n-hexane); hydrochloride (16.2 g.); m.p. 172°–174°C. (from acetonitrile).

EXAMPLE 52

1-(2-Chlorophenyl)-3-(heptanimidoyl)-2-thiourea

Following a procedure similar to that described in Example 42 but using 3.4 g. sodium in 300 ml. acetone, 24.7 g. heptanamidine hydrochloride, and 25.9 g. 2-chlorophenyl isothiocyanate (b.p. 70°–74°C./0.5–1.0 mm.; prepared from 2-chloroaniline) in 125 ml. dry acetone there was obtained 1-(2-chlorophenyl)-3-(heptanimidoyl)-2-thiourea, m.p. 75°–77°C. (from benzene-n-hexane); hydrochloride (33.5 g.), m.p. 158°–160°C. (from acetonitrile).

EXAMPLE 53

1-[4-(Methylthio)phenyl]-3-(heptanimidoyl)-2-thiourea

Following a procedure similar to that described in Example 42 but using 3.4 g. sodium in 500 ml. dry acetone, 24.7 g. heptanamidine hydrochloride, and 27.2 g. 4-(methylthio)phenyl isothiocyanate (m.p. 60°–61°C.; prepared from 4-methylthioaniline) in 120 ml. dry acetone there was obtained 1-[4-(methylthio)phenyl]-3-(heptanimidoyl)-2-thiourea, m.p. 100°–101°C. (from benzene-n-pentane); hydrochloride (43.5 g.), m.p. 181°–182°C.

EXAMPLE 54

1-(4-Iodophenyl)-3-(heptanimidoyl)-2-thiourea

Following a procedure similar to that described in Example 42 but using 2.3 g. sodium in 300 ml. dry acetone, 16.4 g. heptanamidine hydrochloride, and 26.1 g. 4-iodophenyl isothiocyanate (m.p. 75°–78°C.; prepared from 4-iodoaniline) in 150 ml. dry acetone there was obtained 1-(iodophenyl)-3-(heptanimidoyl)-2-thiourea, m.p. 116°–117°C. (from benzene-n-hexane); hydrochloride (28.5 g.), m.p. 185°–187°C. (from isopropyl alcohol).

EXAMPLE 55

1-(3-Chlorophenyl)-3-(heptanimidoyl)-2-thiourea

Following a procedure similar to that described in Example 42 and using 3.4 g. sodium in 450 ml. dry acetone, 24.7 g. heptanamidine hydrochloride, and 25 g. 3-chlorophenyl isothiocyanate (b.p. 64°–65°C./0.4 mm.; prepared from 3-chloroaniline) there was obtained 1-(3-chlorophenyl)-3-heptanimidoyl)-2-thiourea, m.p. 89°–90°C. (from benzene-n-hexane); hydrochloride (34 g.), m.p. 155°–156°C. (from acetonitrile).

EXAMPLE 56

1-[3-(Trifluoromethyl)phenyl]-3-(heptanimidoyl)-2-thiourea

Following a procedure similar to that described in Example 42 and using 3.4 g. sodium in 350 ml. dry acetone, 24.7 g. heptanamidine hydrochloride, and 30.4 g. 3-(trifluoromethyl)phenyl isothiocyanate [b.p. 50°–52°C./0.05–0.08 mm.; prepared from 3-(trifluoromethyl)aniline] in 150 ml. dry acetone there was obtained 1-[3-(trifluoromethyl)phenyl]-3-(heptanimidoyl)-2-thiourea, m.p. 105°–107°C. (from benzene-n-hexane); hydrochloride (34.4 g.), m.p. 154°–155°C. (from acetonitrile).

EXAMPLE 57

1-(2-Chloro-4-methylphenyl)-3-(heptanimidoyl)-2-thiourea

Following a procedure similar to that described in Example 42 and using 2.3 g. sodium in 250 ml. dry acetone, 16.4 g. heptanamidine hydrochloride, and 16 g. 2-chloro-4-methylphenyl isothiocyanate (b.p. 80°–82°C./0.3 mm.; prepared from 2-chloro-4-methylaniline) in 100 ml. dry acetone there was obtained 1-(2-chloro-4-methylphenyl)-3-(heptanimidoyl)-2-thiourea, m.p. 78°–80°C. (from benzene-n-pentane); hydrochloride (23 g.), m.p. 138°–140°C. (from isopropyl alcohol).

EXAMPLE 58

1-[2-Chloro-5-(trifluoromethyl)phenyl]-3-(heptanimidoyl)-2-thiourea

Following a procedure similar to that described in Example 42 but using 1.86 g. sodium in 250 ml. dry acetone, 13.4 g. heptanamidine hydrochloride, and 19.2 g. 2-chloro-5-(trifluoromethyl)phenyl isothiocyanate [prepared from 2-chloro-5-(trifluoromethyl)aniline] in 70 ml. acetone there was obtained 1-[2-chloro-5-(trifluoromethyl)phenyl]-3-(heptanimidoyl)-2-thiourea, m.p. 88°–90°C. (from benzene-n-hexane); hydrochloride (10.3 g.), m.p. 160°–161°C. (from acetonitrile).

EXAMPLE 59

1-[4-(Trifluoromethoxy)phenyl]-3-(heptanimidoyl)-2-thiourea

Following a procedure similar to that described in Example 42 but using 2.3 g. sodium in 300 ml. dry acetone, 16.4 g. heptanimidine hydrochloride, and 21.9 g. 4-(trifluoromethoxy)phenyl isothiocyanate [b.p. 88°C./7 mm.; prepared from 4-(trifluoromethoxy)aniline] in 120 ml. dry acetone there was obtained 1-[4-(trifluoromethoxy)phenyl]-3-(heptanimidoyl)-2-thiourea, m.p. 90°–91°C. (from benzene-n-pentane); hydrochloride (25.3 g.), m.p. 171°–172°C. (from acetonitrile).

EXAMPLE 60

1-(4-Chlorophenyl)-3-(4,4-dimethylpentanimidoyl)-2-thiourea

Following a procedure similar to that described in Example 42 but using 7.22 g. sodium in 705 ml. dry acetone, 51.7 g. 4,4-dimethylvaleramidine hydrochloride, and 53.2 g. 4-chlorophenyl isothiocyanate in 350 ml. dry acetone there was obtained 1-(4-chlorophenyl)-3-(4,4-dimethylpentanimidoyl)-2-thiourea; m.p. 135°–137°C. (from acetonitrile); hydrochloride (80.7 g.), m.p. 182°–186°C.

The 4,4-dimethylvaleramidine hydrochloride (m.p. 268°–270°C.) was obtained by following a procedure similar to that described in Example 11B but using 4,4-dimethylvaleronitrile and ammonia.

The 4,4-dimethylvaleronitrile was prepared as follows:

A mixture of 30.2 g. 3,3-dimethylbutylchloride and 15 g. sodium cyanide in 75 ml. polyethylene glycol was heated at 120°–130°C. for 70 minutes. The mixture was filtered and the filtrate was distilled under reduced pressure to yield 17.4 g. 4,4-dimethylvaleronitrile; b.p. 56°–58°C./14 mm.

EXAMPLE 61

1-(4-Chlorophenyl)-3-(3-ethylpentanimidoyl)-2-thiourea

Following a procedure similar to that described in Example 42 but using 3.8 g. sodium in 350 ml. dry acetone, 27.2 g. 3-ethylvaleramidine hydrochloride, and 27 g. 4-chlorophenyl isothiocyanate in 175 ml. dry acetone there was obtained 1-(4-chlorophenyl)-3-(3-ethylpentanimidoyl)-2-thiourea; m.p. 116°–118°C. (from acetonitrile); hydrochloride (42.7 g.).

The 3-ethylvaleramidine hydrochloride (m.p. 117°–119°C.) was prepared from 3-ethylvaleronitrile (b.p. 64°–66°C./18 mm.) which was prepared from 2-ethylbutylchloride following procedures similar to those described in Example 60.

EXAMPLE 62

1-(4-Chlorophenyl)-3-[11-(dimethylamino)undecanimidoyl]-2-thiourea

Following a procedure similar to that described in Example 42 but using 2.8 g. sodium in 300 ml. dry acetone, 18.5 g. 11-(dimethylamino)undecanamidine dihydrochloride, and 11.9 g. 4-chlorophenyl isothiocyanate in 100 ml. dry acetone there was obtained 10.4 g. 1-(4-chlorophenyl)-3-[11-(dimethylamino)undecanimidoyl]-2-thiourea dihydrochloride; m.p. 130°–132°C. (from isopropyl alcohol).

EXAMPLE 63

1-(4-Chlorophenyl)-3-[5-(dimethylamino)pentanimidoyl]urea

Following a procedure similar to that described in Example 33A but using 1.7 g. sodium in 300 ml. dry acetone, 9 g. 5-(dimethylamino)valeramidine dihydrochloride hemihydrate [m.p. 119°–120°C. (from acetonitrile)], and 5.8 g. 4-chlorophenyl isocyanate in 50 ml. dry acetone there was obtained 8.5 g. 1-(4-chlorophenyl)-3-[5-(dimethylamino)pentanimidoyl]urea dihydrochloride; m.p. 199°–200°C. (from isopropyl alcohol).

EXAMPLE 64

1-(4-Chlorophenyl)-3-[11-(dimethylamino)undecanimidoyl]urea

Following a procedure similar to that described in Example 33A but using 1.97 g. sodium in 300 ml. dry acetone, 13 g. 11-(dimethylamino)undecanamidine dihydrochloride [m.p. 111°–112°C. (from acetonitrile)], and 6.64 g. 4-chlorophenyl isocyanate in 50 ml. dry acetone there was obtained 6.2 g. 1-(4-chlorophenyl)-3-[11-(dimethylamino)undecanimidoyl]urea dihydrochloride hemihydrate, m.p. 140°–142°C. (from acetonitrile).

By following a procedure similar to that described in Example 42 for the preparation of 4-bromophenyl isothiocyanate but substituting for 4-bromoaniline an equivalent amount of the following anilines:
 a. pentachloroaniline
 b. 4-cyanoaniline
 c. 4-butyramidoaniline
 d. 3-hexylthioaniline
 e. 4-sec-butylthioaniline
 f. 4-benzyloxyaniline
 g. 4-diethylaminoaniline
 h. 4-nitroaniline
 i. 2-chloro-5-hexylaniline
 j. 4-bromo-2,6-diiodoaniline
 k. 4-bromo-3-tert-butylaniline
there are obtained respectively the following phenyl isothiocyanates:
 a. pentachlorophenyl isothiocyanate
 b. 4-cyanophenyl isothiocyanate
 c. 4-butyramidophenyl isothiocyanate
 d. 3-hexylthiophenyl isothiocyanate
 e. 4-sec-butylthiophenyl isothiocyanate
 f. 4-benzyloxyphenyl isothiocyanate
 g. 4-diethylaminophenyl isothiocyanate
 h. 4-nitrophenyl isothiocyanate
 i. 2-chloro-5-hexylphenyl isothiocyanate
 j. 4-bromo-2,6-diiodophenyl isothiocyanate
 k. 4-bromo-3-tert-butylphenyl isothiocyanate By following a procedure similar to that described in Example 42 but substituting for 4-bromophenyl isothiocyanate an equivalent amount of the phenyl isothiocyanates listed from a to k inclusive above there are obtained respectively the following imidoylthioureas and their hydrochlorides:
 a. 1-(pentachlorophenyl)-3-(heptanimidoyl)-2-thiourea
 b. 1-(4-cyanophenyl)-3-(heptanimidoyl)-2-thiourea
 c. 1-(4-butyramidophenyl)-3-(heptanimidoyl)-2-thiourea
 d. 1-(3-hexylthiophenyl)-3-(heptanimidoyl)-2-thiourea
 e. 1-(4-sec-butylthiophenyl)-3-(heptanimidoyl)-2-thiourea
 f. 1-(4-benzyloxyphenyl)-3-(heptanimidoyl)-2-thiourea
 g. 1-(4-diethylaminophenyl)-3-(heptanimidoyl)-2-thiourea
 h. 1-(4-nitrophenyl)-3-(heptanimidoyl)-2-thiourea
 i. 1-(2-chloro-5-hexylphenyl)-3-(heptanimidoyl)-2-thiourea
 j. 1-(4-bromo-2,6-diiodophenyl)-3-(heptanimidoyl)-2-thiourea
 k. 1-(4-bromo-3-tert-butylphenyl)-3-(heptanimidoyl)-2-thiourea By following a procedure similar to that described in Example 10 but substituting for 1-(4-nitrophenyl)-3-(pentanimidoyl)urea hydrochloride an equivalent amount of 1-(4-nitrophenyl)-3-(heptanimidoyl)-2-thiourea hydrochloride there is obtained 1-(4-aminophenyl)-3-(heptanimidoyl)-2-thiourea.

By following a procedure similar to that described in Example 19 but substituting for 1-[2-(benzyloxy)phenyl]-3-(pentanimidoyl)urea hydrochloride an equivalent amount of 1-(4-benzyloxyphenyl)-3-(heptanimidoyl)-2-thiourea hydrochloride there is obtained 1-(4-hydroxyphenyl)-3-(heptanimidoyl)-2-thiourea and its hydrochloride.

By following a procedure similar to that described in Example 33C there are obtained respectively from the following:
 a. 13-bromotridecanenitrile
 b. 3-bromobutyronitrile the following:
 a. 13-(dimethylamino)tridecanenitrile
 b. 3-(dimethylamino)butyronitrile By following a procedure similar to that described in Example 33B there can be obtained respectively from the aminonitriles listed from (a) to (b) above and from 2-dimethylaminoacetonitrile the dihydrochlorides of the following:
 a. 13-(dimethylamino)tridecanamidine
 b. 3-(dimethylamino)butyramidine
 c. 2-(dimethylamino)acetamidine By following a procedure similar to that described in Example 62 but substituting for the dihydrochloride of 11-(dimethylamino)undecanamidine and for 4-chlorophenyl isothiocyanate respectively the dihydrochlorides of the amidines and the phenyl isothiocyanates listed below:
 a. 13-(dimethylamino)tridecanamidine and 4-bromo-2,6-diiodophenyl isothiocyanate
 b. 3-(dimethylamino)butyramidine and 4-fluorophenyl isothiocyanate
 c. 2-(dimethylamino)acetamidine and 4-methoxyphenyl isothiocyanate
 d. 4-(diethylamino)butyramidine and 2,4-dinitrophenyl isothiocyanate
 e. 4-(di-n-hexylamino)butyramidine and 4-hexyloxyphenyl isothiocyanate
 f. 4-(dibenzylamino)butyramidine and 3-acetamidophenyl isothiocyanate
 g. 4-(N-methyl-n-hexylamino)butyramidine and 4-acetoxyphenyl isothiocyanate
 h. 4-(1-morpholinyl)butyramidine and 2-isopropoxyphenyl isothiocyanate
 i. 4-(1-thiomorpholinyl)butyramidine and 4-trifluoromethoxyphenyl isothiocyanate
 j. 4-(1-piperidinyl)butyramidine and 4-trifluoromethylphenyl isothiocyanate
 k. 4-(1-pyrrolidinyl)butyramidine and pentachlorophenyl isothiocyanate
there are obtained respectively the dihydrochlorides of the following:
 a. 1-(4-bromo-2,6-diiodophenyl)-3-[13-(dimethylamino)tridecanimidoyl]-2-thiourea
 b. 1-(4-fluorophenyl)-3-[3-(dimethylamino)butyrimidoyl]-2-thiourea
 c. 1-(4-methoxyphenyl)-3-[2-(dimethylamino)acetimidoyl]-2-thiourea
 d. 1-(2,4-dinitrophenyl)-3-[4-(diethylamino)butyrimidoyl]-2-thiourea e. 1-(4-hexyloxyphenyl)-3-[4-(di-n-hexylamino)-butyrimidoyl]-2-thiourea
f. 1-(3-acetamidophenyl)-3-[4-(dibenzylamino)-butyrimidoyl]-2-thiourea
g. 1-(4-acetoxyphenyl)-3-[4-(N-methyl-n-hexylamino)butyrimidoyl]-2-thiourea
h. 1-(2-isopropoxyphenyl)-3-[4-(1-morpholinyl)-butyrimidoyl]-2-thiourea
i. 1-(4-trifluoromethoxyphenyl)-3-[4-(1-thiomorpholinyl)butyrimidoyl]-2-thiourea
j. 1-(4-trifluoromethylphenyl)-3-[4-(1-piperidinyl)-butyrimidoyl]-2-thiourea
k. 1-(pentachlorophenyl)-3-[4-(1-pyrrolidinyl)-butyrimidoyl]-2-thiourea

EXAMPLE 65

1-(3-Chlorophenyl)-3-(pentanimidoyl)-2-thiourea

To a stirred, ice bath chilled solution of 5.4 g. of sodium methoxide in 100 ml. of absolute ethyl alcohol was added slowly 13.69 g. of valeramidine hydrochloride. Stirring was continued for ten minutes and then 16.9 g. of 3-chlorophenyl isothiocyanate was added dropwise and stirring was continued an additional hour. The solvent was evaporated under reduced pressure, the resulting residue was taken up in 100 ml. of dry ether and the ether solution was extracted several times with water and the combined water wash was extracted with 50 ml. dry ether. The combined ether extract was dried and then acidified by addition of 50 ml. 2-N ethereal hydrogen chloride. The resulting precipitate was filtered to give, after recrystallization from acetonitrile, 9.6 g. of 1-(3-chlorophenyl)-3-(pentanimidoyl)-2-thiourea hydrochloride; m.p. 142°–145°C.

EXAMPLE 66

1-[(3-Trifluoromethyl)phenyl]-3-(pentanimidoyl)-2-thiourea

Following a procedure similar to that described in Example 65 but using 3.2 g. of sodium methoxide in 25 ml. of absolute ethyl alcohol, 8.1 g. valeramidine hydrochloride and 12 g. of 3-(trifluoromethyl)phenyl isothiocyanate, there was obtained, after recrystallization from acetonitrile, 11.0 g. of 1-[(3-trifluoromethyl)phenyl]-3-(pentanimidoyl)-2-thiourea hydrochloride; m.p. 143°–147°C.

EXAMPLE 67

1-(3,5-Dichlorophenyl)-3-(pentanimidoyl)-2-thiourea

Following a procedure similar to that described in Example 65 but using 5.4 g. of sodium methoxide in 100 ml. of absolute ethyl alcohol, 13.6 g. of valeramidine hydrochloride and 20.4 g. of 3,5-dichlorophenyl isothiocyanate, there was obtained, after recrystallization from isopropyl alcohol, 12.6 g. of 1-(3,5-dichlorophenyl)-3-(pentanimidoyl)-2-thiourea hydrochloride; m.p. 144°–146°C.

EXAMPLE 68

1-(3,4-Dichlorophenyl)-3-(pentanimidoyl)-2-thiourea

Following a procedure similar to that described in Example 65 but using 5.4 g. of sodium methoxide in 100 ml. of absolute ethyl alcohol, 13.6 g. valeramidine hydrochloride and 20.4 g. of 3,4-dichlorophenyl isothiocyanate, there was obtained, after recrystallization from isopropyl alcohol, 5.0 g. of 1-(3,4-dichlorophenyl)-3-(pentanimidoyl)-2-thiourea hydrochloride; m.p. 111°–113°C.

I claim:
1. 1-(4-Nitrophenyl)-3-(pentanimidoyl)urea.
2. 1-(2-Nitrophenyl)-3-(pentanimidoyl)urea.
3. 1-[3-(Trifluoromethyl)phenyl]-3-(pentanimidoyl)urea.
4. 1-[2-(Benzyloxy)phenyl]-3-(pentanimidoyl)urea.
5. 1-(4-Aminophenyl)-3-(pentanimidoyl)urea.

* * * * *